us009968534B2

(12) United States Patent
Greaves

(10) Patent No.: US 9,968,534 B2
(45) Date of Patent: May 15, 2018

(54) ANIONIC DIRECT DYE HAVING A TETRAALKYLAMMONIUM COUNTERION, DYEING COMPOSITION COMPRISING THEM AND METHOD FOR DYEING KERATINOUS FIBRES STARTING FROM THESE DYES

(75) Inventor: Andrew Greaves, Magny-le-hongre (FR)

(73) Assignee: L'OREAL, Paris (FR)

( * ) Notice: Subject to any disclaimer, the term of this patent is extended or adjusted under 35 U.S.C. 154(b) by 0 days. days.

(21) Appl. No.: 13/988,153

(22) PCT Filed: Nov. 16, 2011

(86) PCT No.: PCT/EP2011/070234
§ 371 (c)(1),
(2), (4) Date: May 17, 2013

(87) PCT Pub. No.: WO2012/066028
PCT Pub. Date: May 24, 2012

(65) Prior Publication Data
US 2013/0227797 A1    Sep. 5, 2013

Related U.S. Application Data

(60) Provisional application No. 61/418,493, filed on Dec. 1, 2010.

(30) Foreign Application Priority Data

Nov. 18, 2010  (FR) .................... 10 59475

(51) Int. Cl.
| | | |
|---|---|---|
| A61Q 5/10 | (2006.01) | |
| A61K 8/41 | (2006.01) | |
| A61K 8/46 | (2006.01) | |
| A61K 8/49 | (2006.01) | |
| A61Q 5/06 | (2006.01) | |
| C09B 69/04 | (2006.01) | |

(52) U.S. Cl.
CPC .............. *A61K 8/416* (2013.01); *A61K 8/466* (2013.01); *A61K 8/494* (2013.01); *A61K 8/4946* (2013.01); *A61Q 5/065* (2013.01); *A61Q 5/10* (2013.01); *C09B 69/04* (2013.01); *C09B 69/045* (2013.01)

(58) Field of Classification Search
CPC .......... A61Q 5/065; A61Q 5/10; A61K 8/416; A61K 8/466; C09B 27/00; C09B 43/00; C09B 43/085; C09B 44/02; C09B 69/045; C09B 29/00; C09B 29/16; C09B 29/30; C09B 69/04
USPC ....................... 8/405, 641, 642; 534/784, 882
See application file for complete search history.

(56) References Cited

U.S. PATENT DOCUMENTS

| | | |
|---|---|---|
| 5,980,587 A | 11/1999 | Samain |
| 6,368,360 B2 | 4/2002 | Samain |
| 2001/0001333 A1 | 5/2001 | Samain |
| 2006/0053571 A1 | 3/2006 | Feiler et al. |
| 2008/0184497 A1 | 8/2008 | Ruch et al. |

FOREIGN PATENT DOCUMENTS

| | | | | |
|---|---|---|---|---|
| DE | 3434920 | | 5/1986 | |
| EP | 0553705 | | 8/1993 | |
| EP | 0553705 A1 | * | 8/1993 | ............. C09B 67/24 |
| FR | 2741798 | | 6/1997 | |
| JP | 0814335 | * | 6/1996 | ............... A61K 7/13 |
| WO | 00/38631 | | 7/2000 | |
| WO | 2007/071685 | | 6/2007 | |

OTHER PUBLICATIONS

STIC Search Report dated Dec. 4, 2013.*
International Search Report and Written Opinion for PCT/EP2011/070234.
PCT/IB/308 form for PCT/EP2011/070234.
"Hair Preparation," Kirk Othmer Encyclopedia of Chemical Technoloty, pt. 4, p. 18; published online Sep. 18, 2009, DOI: 10.1002/0471238961.0801091816150812.a01.pub2.
"Hair Preparation," Ullmann's Encyclopedia of Industrial Chemistry, pt. 5.2.3, p. 21, published online: Jul. 15, 2006, DOI: 10.1002/14356007.a12_571.pub.
"Azo Dyes," Ullmann's Encyclopedia of Industrial Chemistry, 2005, Wiley-VCH Verlag GmbH & Co. KGaA, Weinheim, 10.1002/14356007.a03 245, point 3.2.
"Textile Auxiliaries," Ullmann's Encyclopedia of Industrial Chemistry, 2002, Wiley-VCH Verlag GmbH & Co. KGaA, Weinheim, 10.1002/14356007.a26 227.
Ashford's Dictionary of Industrial Chemicals, Second Edition, 2001, pp. 14-39.

(Continued)

*Primary Examiner* — Eisa B Elhilo
(74) *Attorney, Agent, or Firm* — The Marbury Law Group, PLLC

(57) ABSTRACT

The invention relates to the dyeing of human keratinous fibers, in particular the hair, using anionic direct dyes or acid dyes having a tetraalkylammonium counterion of formula (I), with $Col^{(-)}m$, $R_1$, $R_2$, $R_3$, $R_4$, m, and n as defined in the description. A subject-matter of the invention is a dyeing composition comprising an anionic dye of formula (I) and a method for dyeing keratinous fibers, such as the hair, employing the said composition. A subject-matter of the invention is likewise novel dyes of formula (I) and their uses for the coloring of keratinous fibers. This composition makes it possible to obtain a chromatic, powerful and particularly persistent coloring on keratinous fibers.

(I)

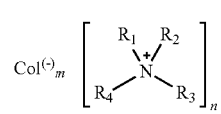

18 Claims, No Drawings

(56) References Cited

OTHER PUBLICATIONS http://www.sigmaaldrich.com/analytical-chromatography/sample-preparation/spe/ionexchange-methodology.html.
Dardel, F. et al., "Ion Exchange," Ullmann's Encyclopedia of Industrial Chemistry, published online Apr. 15, 2008, DOI: 10.1002/14356007.a14_393.pub 2, pp. 474-545.
Dickert, C., "Ion Exchange," Kirk-Othmer Encyclopedia of Chemical Technology, published online Apr. 12, 2000, DOI: 10.1002/0471238961.09151404090311.a01, pp. 1-31.

* cited by examiner

ANIONIC DIRECT DYE HAVING A TETRAALKYLAMMONIUM COUNTERION, DYEING COMPOSITION COMPRISING THEM AND METHOD FOR DYEING KERATINOUS FIBRES STARTING FROM THESE DYES

This is a national stage application of PCT/EP2011/070234, filed internationally on Nov. 16, 2011, which claims priority to U.S. Provisional Application No. 61/418,493, filed on Dec. 1, 2010; as well as French Application FR 1059475, filed on Nov. 18, 2010.

The invention relates to the dyeing of human keratinous fibres using anionic direct dyes having a tetraalkylammonium counterion.

It is known to dye keratinous fibres, in particular the hair, by direct dyeing. The method conventionally used in direct dyeing consists in applying, to the keratinous fibres, direct dyes, which are coloured and colouring molecules having an affinity for fibres, in allowing them to diffuse and in then rinsing the fibres.

The direct dyes which are conventionally used are, for example, dyes of the nitrobenzene type, anthraquinone dyes, nitropyridines or dyes of the azo, xanthene, acridine, azine or triarylmethane type. These dyes can be anionic, cationic or neutral. Anionic dyes or "acid dyes" are known not to be persistent on keratinous fibres and to have a low colouring power. In addition, they are easily absorbed by the skin as the hair, which has the effect of colouring the scalp when the hair is dyed. For these reasons, anionic dyes are not used to any great extent as dye for hair dyeing (see, for example, *Kirk Othmer Encyclopedia of Chemical Technology*—"Hair Preparation", pt. 4, p. 18; Published Online 18 Sep. 2009, DOI: 10.1002/0471238961.0801091816150812.a01.pub2; *Ullmann's Encyclopedia of Industrial Chemistry*, "Hair Preparation", pt. 5.2.3, p. 21; Published Online: 15 Jul. 2006, DOI: 10.1002/14356007.a12_571.pub2).

The aim of the present invention is to provide novel dyes for human keratinous fibres, such as the hair, which exhibit improved dyeing properties, in particular a colouring of the hair which is powerful, chromatic and/or persistent with regard to external attacks, in particular to shampooing operations, without causing excessive staining of the scalp. The invention is also targeted at making available hair dyes with a low colouring selectivity between the root and the tip, which do not damage the keratinous fibres, which do not detrimentally affect their cosmetic properties and which produce less staining of the skin.

These aims are achieved by the present invention, a subject-matter of which is a method for dyeing keratinous fibres which consists in applying, to the said fibres, a composition comprising one or more anionic dyes of formula (I):

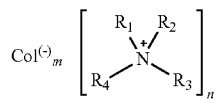

(I)

and their optical isomers, geometric isomers and solvates, such as hydrates; in which formula (I):
  $R_1$, $R_2$, $R_3$ and $R_4$, which are identical or different, represent a group chosen from i) $(C_1-C_{20})$alkyl; ii) $(C_2-C_{20})$alkenyl; it being possible for the alkyl or alkenyl group of the groups of i) and ii) to be interrupted by one or more identical or different heteroatoms chosen from oxygen, sulphur or $N(R\alpha)$, with $R\alpha$ representing a hydrogen atom or an alkyl group; preferably, $R_1$, $R_2$, $R_3$ and $R_4$ are identical and more particularly represent a linear $(C_1-C_5)$alkyl group, such as methyl, ethyl, propyl or butyl;
  $Col^{(-)}_m$ represents the anionic part of the anionic direct dye or acid dye comprising, in its structure, at least one sulphonate group and/or at least one carboxylate group and comprising m anionic charge(s);
  m and n, which are identical or different, represent an integer between 1 and 10 inclusive;
it being understood that:
  when the anionic part of the anionic direct dye comprises a sulphonate group or a carboxylate group, then m=n=1; and
  when the anionic part of the anionic direct dye comprises anionic groups other than the sulphonate or carboxylate group, it is combined with one or more cationic counterions, organic, inorganic or $R_1R_2R_3R_4N^+$, making it possible to achieve electrical neutrality of the formula (I).

Another subject-matter of the invention is the use of at least one anionic dye of formula (I) as defined above to dye keratinous fibres, such as the hair.

Another subject-matter of the invention is the use of at least one fluorescent anionic dye of formula (I), particularly in the range of the orangey colours, for the purpose of optically lightening dark keratinous fibres, such as hair with a height of tone of less than or equal to 6 and preferably of less than or equal to 4, this being achieved even in the absence of a chemical oxidizing agent other than atmospheric oxygen.

Another subject-matter of the invention is a method for dyeing keratinous fibres employing one or more anionic dyes of formula (I) as defined above.

Another subject-matter of the invention is an anionic dye of formula (I) as described above; preferably, the said dye of formula (I) is such that the $R_1$, $R_2$, $R_3$ and $R_4$ radicals are identical and the said dye of formula (I) is different from the dyes of following formulae (a) to (u):

(a)

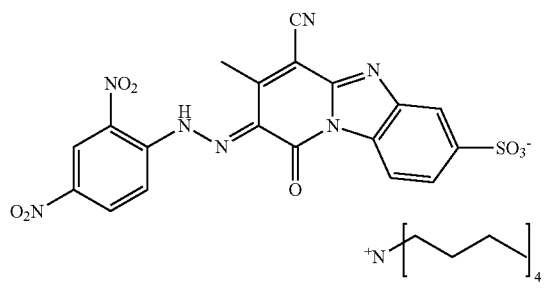

(b)

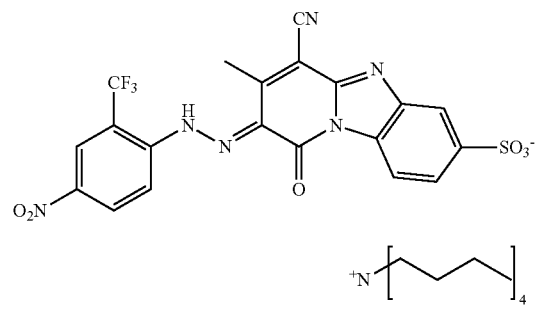

-continued
(c)
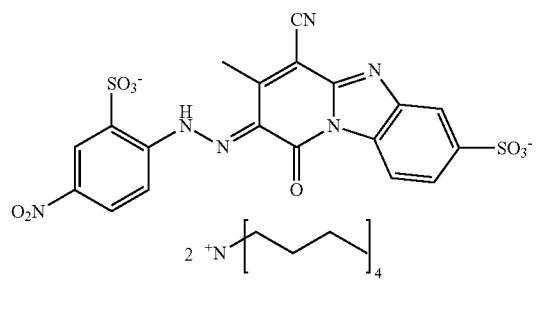
(d)
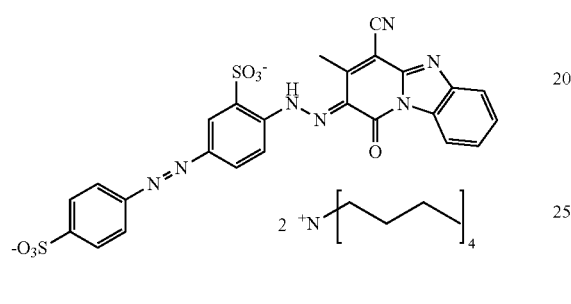
(e)
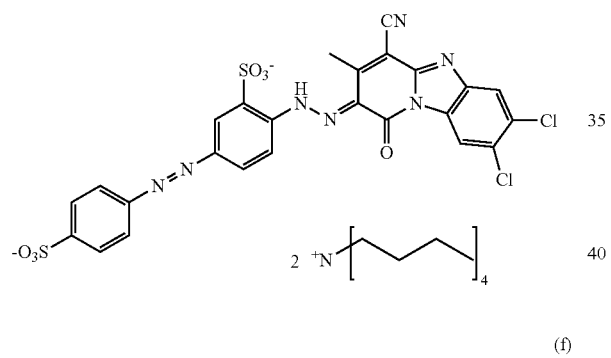
(f)
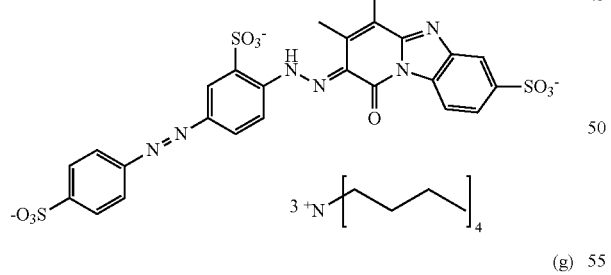
(g)
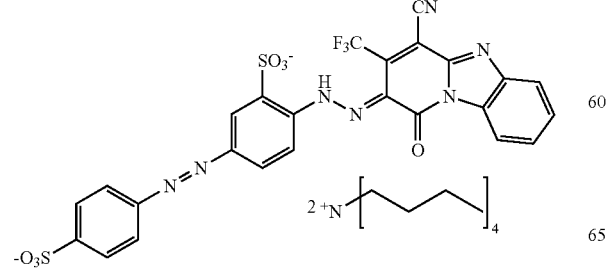
(h)
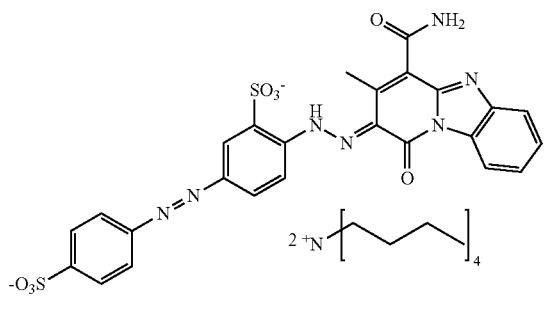
(i)
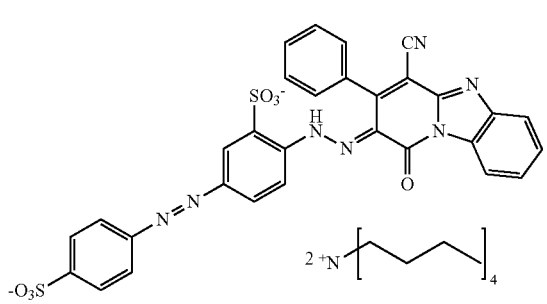
(j)
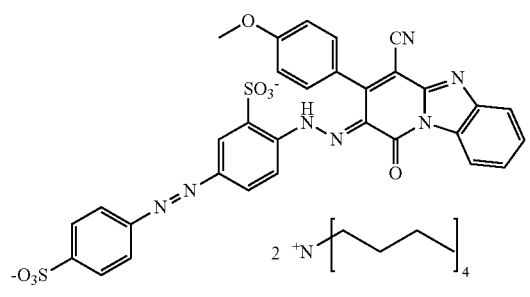
(k)
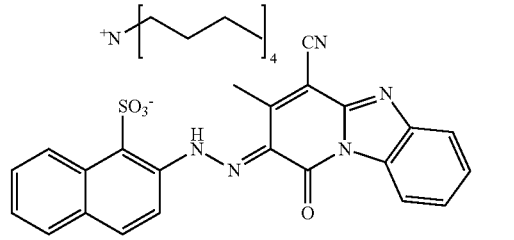
(l)
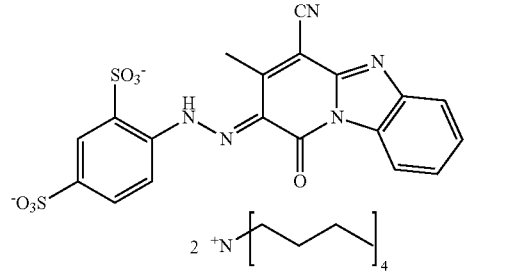

(m)
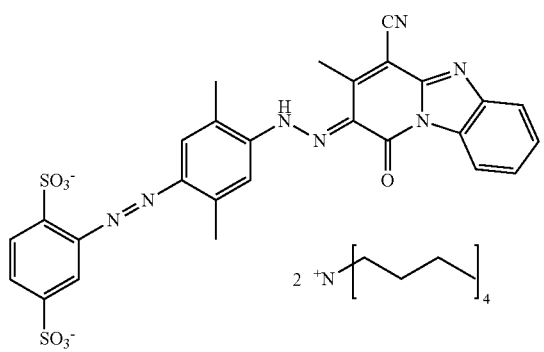

(n)
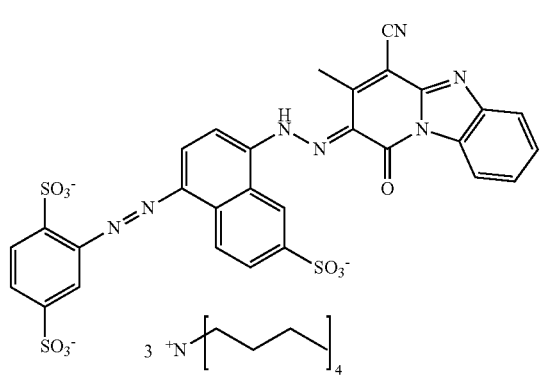

(o)
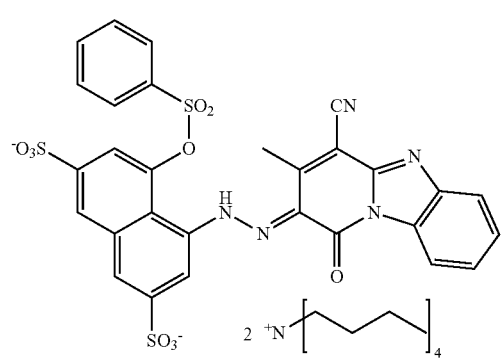

(p)
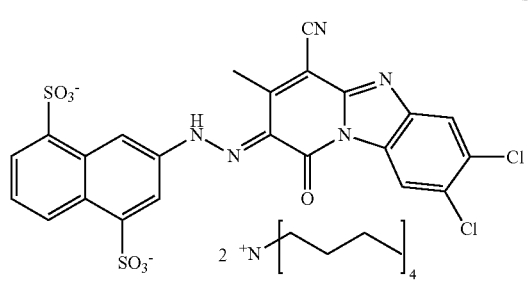

(q)
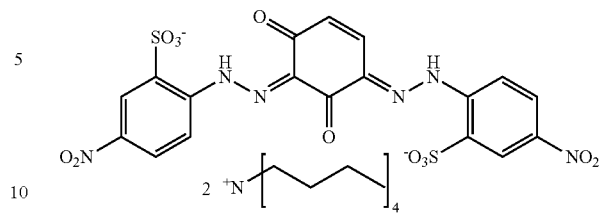

(r)
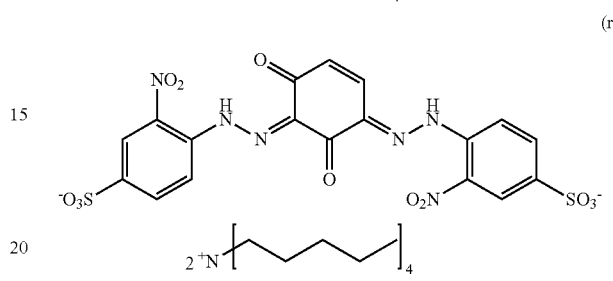

(s)
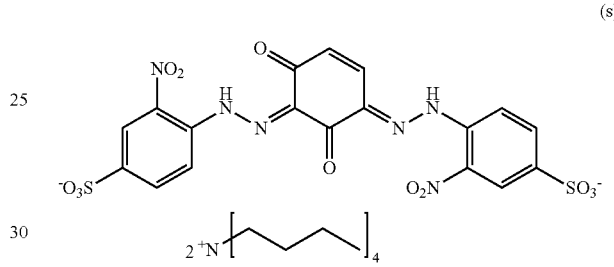

(t)
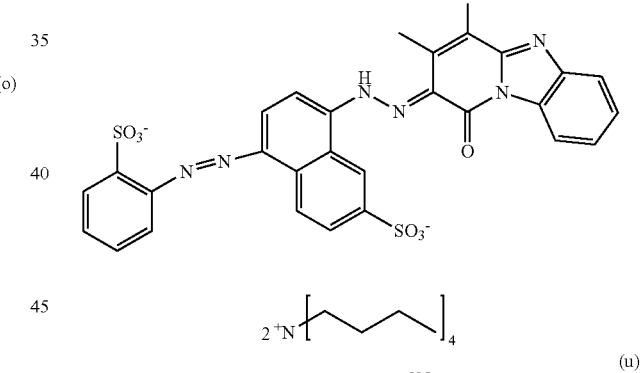

(u)
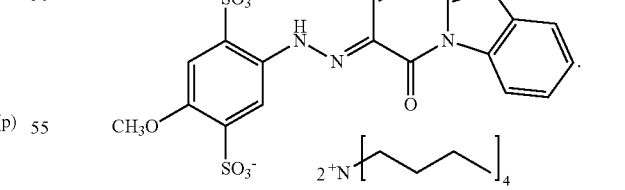

Another subject-matter of the invention is a dyeing composition comprising, in an appropriate cosmetic medium, at least one anionic dye of formula (I); preferably, the said anionic dye of formula (I) is such that the $R_1$, $R_2$, $R_3$ and $R_4$ radicals are identical, and the said dye of formula (I) is different from the dyes of formulae (a) to (u) as defined above.

With the dyes of the invention, it is possible to improve the dyeing properties of anionic dyes, in particular in terms of chromaticity, power and persistence, by replacing "conventional" cationic counterions, such as alkali metal or alkaline earth metal cations, by an organic cation of tetraalkylammonium type, preferably having a $C_1$-$C_6$ chain, such as butyl.

The anionic dyes of formula (I) according to the invention are furthermore stable with regard to oxidizing agents and exhibit a satisfactory solubility in cosmetic dyeing media.

The term "dark hair" is understood to mean hair which is naturally or artificially dark and which has a height of tone of less than or equal to 6 (dark blond) and preferably of less than or equal to 4 (chestnut). The notion of "tone" is based on the classification of natural hues, one tone separating each hue from that which immediately follows or precedes it. This definition and the classification of natural hues are well known to professionals in hairstyling and are published in the work "Science des traitements capillaries" [The Science of Hair Care] by Charles Zviak, 1988, published by Masson, pp. 215 and 278. The heights of tone range from 1 (black) to 10 (very light blonde), one unit corresponding to one tone; the higher the figure, the lighter the hue.

Within the meaning of the present invention and unless otherwise indicated:
- the "aryl" or "heteroaryl" radicals or the aryl or heteroaryl part of a radical can be substituted by at least one substituent carried by a carbon atom chosen from:
  - a $C_1$-$C_{16}$, preferably $C_1$-$C_8$, alkyl radical optionally substituted by one or more radicals chosen from hydroxyl, $C_1$-$C_2$ alkoxy, $C_2$-$C_4$(poly)hydroxyalkoxy, acylamino or substituted amino radicals, the substituted amino radical being substituted by two identical or different $C_1$-$C_4$ alkyl radicals optionally carrying at least one hydroxyl group or it being possible for the two radicals to form, with the nitrogen atom to which they are attached, a saturated or unsaturated 5- to 7-membered, preferably 5- or 6-membered, heterocycle which is optionally substituted and which optionally comprises another heteroatom identical to or different from nitrogen;
  - a halogen atom, such as chlorine, fluorine or bromine;
  - a hydroxyl group;
  - a $C_1$-$C_2$ alkoxy radical;
  - a $C_2$-$C_4$ (poly)hydroxyalkoxy radical;
  - an amino radical;
  - a nitro radical;
  - a 5- or 6-membered heterocycloalkyl radical;
  - an optionally cationic 5- or 6-membered heteroaryl radical, preferably an imidazolium radical, which is optionally substituted by a ($C_1$-$C_4$)alkyl radical, preferably a methyl radical;
  - an amino radical substituted by one or two identical or different $C_1$-$C_6$ alkyl radicals which optionally carry at least
    i) one hydroxyl group,
    ii) one amino group optionally substituted by one or two $C_1$-$C_3$ alkyl radicals which are optionally substituted, it being possible for the said alkyl radicals to form, with the nitrogen atom to which they are attached, a saturated or unsaturated 5- to 7-membered heterocycle which is optionally substituted and which optionally comprises at least one other heteroatom identical to or different from nitrogen,
  - an acylamino (—NR—C(O)R') radical, in which the R radical is a hydrogen atom or a $C_1$-$C_4$ alkyl radical optionally carrying at least one hydroxyl group and the R' radical is a $C_1$-$C_2$ alkyl radical;
  - a carbamoyl (($R)_2$N—C(O)—) radical, in which the R radicals, which are identical or different, represent a hydrogen atom or a $C_1$-$C_4$ alkyl radical optionally carrying at least one hydroxyl group;
  - a carboxylic acid or ester (—O—C(O)R' or —C(O)OR') radical, in which the R' radical is a hydrogen atom or a $C_1$-$C_4$ alkyl radical optionally carrying at least one hydroxyl group and the R' radical is a $C_1$-$C_2$ alkyl radical;
  - it being possible for the carboxyl radical to be in the acid or salified form (preferably salified with an alkali metal or a substituted or unsubstituted ammonium);
  - an alkylsulphonylamino (R'$SO_2$—NR—) radical, in which the R radical represents a hydrogen atom or a $C_1$-$C_4$ alkyl radical optionally carrying at least one hydroxyl group and the R' radical represents a $C_1$-$C_4$ alkyl radical or a phenyl radical;
  - an aminosulphonyl (($R)_2$N—$SO_2$—) radical, in which the R radicals, which are identical or different, represent a hydrogen atom or a $C_1$-$C_4$ alkyl radical optionally carrying at least one hydroxyl group,
  - a cyano (CN) group;
  - a (poly)haloalkyl group, preferably trifluoromethyl ($CF_3$);
- the cyclic or heterocyclic part of a nonaromatic radical can be substituted by at least one substituent carried by a carbon atom chosen from the following groups:
  - hydroxyl;
  - $C_1$-$C_4$ alkoxy or $C_2$-$C_4$ (poly)hydroxyalkoxy;
  - alkylcarbonylamino (RC(O)—NR'—), in which the R' radical is a hydrogen atom or a $C_1$-$C_4$ alkyl radical optionally carrying at least one hydroxyl group and the R radical is a $C_1$-$C_2$ alkyl radical or an amino radical substituted by two identical or different $C_1$-$C_4$ alkyl groups optionally carrying at least one hydroxyl group, it being possible for the said alkyl radicals to form, with the nitrogen atom to which they are attached, a saturated or unsaturated 5- to 7-membered heterocycle which is optionally substituted and which optionally comprises at least one other heteroatom identical to or different from nitrogen;
  - alkylcarbonyloxy (RC(O)—O—), in which the R radical is a $C_1$-$C_4$ alkyl radical or an amino radical substituted by two identical or different $C_1$-$C_4$ alkyl groups optionally carrying at least one hydroxyl group, it being possible for the said alkyl radicals to form, with the nitrogen atom to which they are attached, a saturated or unsaturated 5- to 7-membered heterocycle which is optionally substituted and which optionally comprises at least one other heteroatom identical to or different from nitrogen;
  - alkoxycarbonyl (RO—C(O)—), in which the R radical is a $C_1$-$C_4$ alkyl radical or an amino radical substituted by two identical or different $C_1$-$C_4$ alkyl groups optionally carrying at least one hydroxyl group, it being possible for the said alkyl radicals to form, with the nitrogen atom to which they are attached, a saturated or unsaturated 5- to 7-membered heterocycle which is optionally substituted and which optionally comprises at least one other heteroatom identical to or different from nitrogen;

a cyclic or heterocyclic radical or a nonaromatic part of an aryl or heteroaryl radical can also be substituted by one or more oxo groups;

an "aryl" radical represents a monocyclic or fused or nonfused polycyclic group comprising from 6 to 22 carbon atoms, at least one ring of which is aromatic; in particular, the aryl radical is a phenyl, biphenyl, naphthyl, indenyl, anthracenyl or tetrahydronaphthyl and more preferably phenyl;

a "heteroaryl" radical represents a monocyclic or fused or nonfused polycyclic group comprising from 5 to 22 ring members and from 1 to 6 heteroatoms chosen from nitrogen, oxygen, sulphur and selenium atoms, at least one ring of which is aromatic; preferably, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenooxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl and xanthyl and its ammonium salt;

a "cyclic" radical is a "cycloalkyl" radical, i.e. a monocyclic or fused or nonfused nonaromatic radical which comprises from 5 to 22 carbon atoms and which can comprise from one to several unsaturations, such as cyclohexyl or cyclopentyl;

a "heterocyclic" radical is a monocyclic or fused or nonfused polycyclic nonaromatic radical which comprises from 5 to 22 ring members and which comprises from 1 to 6 heteroatoms chosen from nitrogen, oxygen, sulphur and selenium atoms, morpholinyl, thiomorpholinyl, piperidinyl, piperazinyl, pyrrolidinyl, tetrahydrofuranyl, tetrahydrothiophenyl, azepanyl, thioazepanyl; preferably pyrrolidinyl and morpholino;

an "alkyl" radical is a linear or branched $C_1$-$C_{16}$, preferably $C_1$-$C_8$ and in particular $C_1$-$C_4$ hydrocarbon radical, such as methyl or ethyl;

an "alkenyl" radical is a linear or branched $C_2$-$C_{20}$ hydrocarbon radical comprising one or more conjugated or nonconjugated double bonds, in particular a $C_4$-$C_{10}$ hydrocarbon radical comprising one, two or three double bonds, preferably a single double bond;

the expression "optionally substituted" assigned to the alkyl radical implies that the said alkyl radical can be substituted by one or more radicals chosen from the following radicals: i) hydroxyl, ii) $C_1$-$C_4$ alkoxy, iii) acylamino, iv) amino optionally substituted by one or two identical or different $C_1$-$C_4$ alkyl radicals, it being possible for the said alkyl radicals to form, with the nitrogen atom which carries them, a 5- to 7-membered heterocycle optionally comprising another heteroatom identical to or different from nitrogen;

an "alkoxy" radical is an alkyl-oxy or alkyl-O— radical for which the alkyl radical is a linear or branched $C_1$-$C_{16}$, preferably $C_1$-$C_8$ and in particular $C_1$-$C_4$ hydrocarbon radical, such as methoxy or ethoxy, and, when the alkoxy group is optionally substituted, this implies that the alkyl group is optionally substituted as defined above;

a "(poly)haloalkyl" radical is an "alkyl" radical as defined above in which one or more hydrogen atoms are substituted or replaced by one or more halogen atoms, such as fluorine, chlorine or bromine atoms; mention may be made, as polyhaloalkyl, of the trifluoromethyl group;

an "alkylthio" radical is an alkyl-S— radical for which the alkyl radical is a linear or branched $C_1$-$C_{16}$, preferably $C_1$-$C_8$ and in particular $C_1$-$C_4$ hydrocarbon radical, such as methylthio or ethylthio, and, when the alkylthio group is optionally substituted, this implies that the alkyl group is optionally substituted as defined above;

a cationic counterion is organic or inorganic preferably chosen from alkali metal or alkaline earth metal inorganic cations, such as Na, Mg, K and Ca, and organic cations, such as ammonium $NH_4^+$;

when the expression "at least one" is employed, this implies "one or more".

Furthermore, unless otherwise indicated, the limits delimiting the extent of a range of values are included within this range of values.

According to the present invention, the term "dye" is understood to mean a compound which has the ability to dye and which is provided as a coloured compound observable by eye, i.e. which absorbs light at a wavelength included in UV and visible radiation, at a wavelength $\lambda_{abs}$ of between 250 and 800 nm, particularly in the visible spectrum between 400 and 700 nm.

The term "fluorescent dye" is understood to mean a dye as defined above which, in addition to the fact of being coloured, is fluorescent, that is to say that it has the ability to reemit at least a portion of the light absorbed in the visible region at a greater wavelength than that absorbed. In particular, the fluorescent dye is capable of absorbing UV or visible radiation at a wavelength $\lambda_{abs}$ of between 250 and 800 nm and of reemitting in the visible region at an emission wavelength $\lambda_{em}$ of between 400 and 800 nm. Preferably, the fluorescent dye is a dye in the range of the orangey colours.

I. Dyes of Formula (I)

The anionic direct dyes of formula (I) according to the invention "result" from dyes commonly known as "acid dyes" for their affinity with alkaline substances (see, for example, "*Industrial Dyes*, Chemistry, Properties, Application ", edited by Klaus Hunger, Wiley-VCH Verlag GmbH & Co. KGaA, Weinheim, 2003). Acid or anionic dyes are known in the literature (see, for example "*Ullman's Encyclopedia of Industrial Chemistry*", Azo Dyes, 2005, Wiley-VCH Verlag GmbH & Co. KGaA, Weinheim, 10.1002/14356007.a03 245, point 3.2; ibid, Textile Auxiliaries, 2002, Wiley-VCH Verlag GmbH & Co. KGaA, Weinheim, 10.1002/14356007.a26 227, and "*Ashford's* Dictionary of Industrial Chemicals, Second Edition ", p. 14-p. 39, 2001).

The term "anionic direct dyes" is understood to mean any direct dye comprising, in its structure, at least one sulphonate group $SO_3^-$ and/or at least one carboxylate group $C(O)O^-$ and optionally one or more anionic groups $G^-$, with $G^-$, which are identical or different, representing an anionic group chosen from alkoxide $O^-$, thiolate $S^{31}$, carboxylate and thiocarboxylate: $C(Q)Q'^-$, with Q and Q', which are identical or different, representing an oxygen or sulphur atom; preferably, G⁻ represents a carboxylate, i.e. Q and Q' represent an oxygen atom.

In the formula (I) of the invention, the $Col^{(-)}{}_m$ radical represents the anionic part of the "acid dyes" or of the anionic direct dyes which "results" from the said acid dyes or from the said anionic direct dyes. The dyes of the invention resulting from the said acid dyes or from the said anionic direct dyes thus comprise at least one $R_1R_2R_3R_4N^+$ cationic counterion as defined above; preferably tetrabutylammonium.

Preferably, $Col^{(-)}{}_m$ comprises, in its structure:
at least one sulphonate group and at least one (hetero)aryl group, it being understood that at least one sulphonate group is directly connected to a (hetero)aryl group, preferably an aryl group, such as phenyl or benzo; and
optionally one or more anionic groups $G^{31}$, as defined above.

According to another preferred embodiment of the invention, $Col^{(-)}{}_m$ comprises, in its structure:
at least one carboxylate group and at least one (hetero)aryl group, it being understood that at least one carboxylate group is directly connected to a (hetero)aryl group, preferably an aryl group, such as phenyl or benzo; and
optionally one or more anionic groups $G^{31}$, as defined above.

According to yet another preferred embodiment of the invention, $Col^{(-)}{}_m$ comprises, in its structure:
at least one sulphonate group, at least one carboxylate group and at least one (hetero)aryl group, it being understood that at least one sulphonate or carboxylate group is directly connected to a (hetero)aryl group, preferably an aryl group, such as phenyl or benzo; and
optionally one or more anionic groups G⁻, as defined above.

According to a specific embodiment of the invention, the dyes of formula (I) are such that m is equal to n.

An advantageous alternative form of the invention relates to the dyes of formula (I) for which m and n have the values 1, 2 or 3.

Preferably, when compound of formula (I) according to the invention is derived from hydrazono anionic dyes thus it neither comprise a 1,5-dioxocyclohex-2-enyl group nor a benzimidazolopyridone group. More preferably, compound of formula (I) does not bear a hydrazono group.

The preferred anionic dyes of formula (I) of the invention are chosen from acid nitro direct dyes, acid azo dyes, acid azine dyes, acid triarylmethane dyes, acid indoamine dyes, acid anthraquinone dyes, indigoids and acid natural dyes, each of these dyes having at least one sulphonate or carboxylate group having a cationic counterion $R_1R_2R_3R_4N^+$ as defined above; preferably tetrabutylammonium sulphonate or carboxylate.

According to a specific form of the invention, the ammonium counterion of the dye of formula (I) of the invention is such that the $R_1$, $R_2$, $R_3$ and $R_4$ radicals are identical.

According to another advantageous embodiment of the invention, $R_1$, $R_2$, $R_3$ and $R_4$ are linear.

According to another specific form of the invention, $R_1$, $R_2$, $R_3$ and $R_4$ are chosen from i) $(C_1-C_6)$alkyl; ii) $(C_2-C_6)$alkenyl; it being possible for the alkyl or alkenyl group of the groups of i) and ii) to be interrupted by one or more identical or different heteroatoms chosen from oxygen, sulphur or $N(R\alpha)$, with $R\alpha$ representing a hydrogen atom or an alkyl group; preferably, $R_1$, $R_2$, $R_3$ and $R_4$ are identical and more particularly represent a linear $(C_1-C_6)$alkyl group, such as methyl, ethyl, propyl or butyl.

According to yet another specific form of the invention, $R_1$, $R_2$, $R_3$ and $R_4$ are fatty chains, i.e. chosen from i) $(C_8-C_{20})$alkyl; ii) $(C_8-C_{20})$alkenyl; it being possible for the alkyl or alkenyl group of the groups of i) and ii) to be interrupted by one or more identical or different heteroatoms chosen from oxygen, sulphur or $N(R\alpha)$, with $R\alpha$ representing a hydrogen atom or an alkyl group; preferably, $R_1$, $R_2$, $R_3$ and $R_4$ are identical and more particularly represent a linear $(C_8-C_{20})$alkyl group.

Mention may be made, as anionic dyes according to the invention, of the dyes of following formulae (II), (II'), (III), (III'), (IV), (IV'), (V), (V'), (VI), (VII), (VIII) and (IX):

a) Diaryl Anionic Azo Dyes of Formula (II) or (II'):

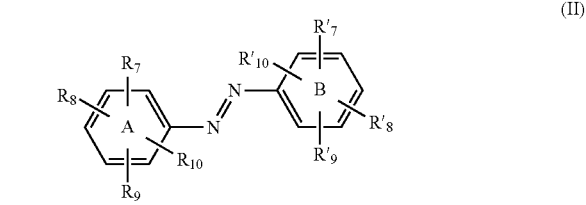

(II)

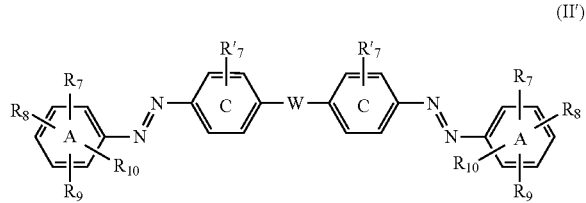

(II')

in which formulae (II) and (II'):
$R_7$, $R_8$, $R_9$, $R_{10}$, $R'_7$, $R'_8$, $R'_9$ and $R'_{10}$, which are identical or different, represent a hydrogen atom or a group chosen from:
alkyl;
alkoxy, alkylthio;
hydroxyl, mercapto;
nitro;
$R°$—C(X)—X'—, $R°$—X'—C(X)—, $R°$—X'—C(X)—X"—, with $R°$ representing a hydrogen atom or an alkyl or aryl group; X, X' and X", which are identical or different, representing an oxygen or sulphur atom or NR, with R representing a hydrogen atom or an alkyl group;
$M^+(O)_2S(O^-)$—, with $M^+$ as defined above for $M^+$ or representing a cationic counterion $R_1R_2R_3R_4N^+$ as defined above;
$M^+(O)CO$—, with $M^+$ as defined above;
R"—S(O)$_2$—, with R" representing a hydrogen atom or an alkyl, aryl, (di)(alkyl)amino or aryl(alkyl)amino group; preferably, a phenylamino or phenyl group;
R'''—S(O)$_2$—X'—, with R''' representing an alkyl group or an aryl group which is optionally substituted, and X' as defined above;
(di)(alkyl)amino;
aryl(alkyl)amino, optionally substituted by one or more groups chosen from i) nitro; ii) nitroso; iii) $M^+(O)_2S(O^-)$— and iv) alkoxy, with $M^+$ as defined above;

optionally substituted heteroaryl; preferably, a benzothiazolyl group;
cycloalkyl; in particular cyclohexyl;
Ar—N═N—, with Ar representing an optionally substituted aryl group; preferably, a phenyl optionally substituted by one or more alkyl, $M^+(O)_2S(O^-)$— or phenylamino groups;
or else two contiguous groups, $R_7$ with $R_8$ or $R_8$ with $R_9$ or $R_9$ with $R_{10}$, together form a fused benzo group A';
and $R'_7$ with $R'_8$ or $R_8$ with $R_9$, or $R_9$, with $R'_{10}$ together form a fused benzo group B'; with A' and B' optionally substituted by one or more groups chosen from i) nitro; ii) nitroso; iii) $M^+(O)_2S(O^-)$—; iv) hydroxyl; v) mercapto; vi) (di)(alkyl)amino; vii) $R°—C(X)—X'—$; viii) $R°—X'—C(X)—$; ix) $R°—X'—C(X)—X''—$; x) Ar—N═N— and xi) aryl (alkyl)amino which is optionally substituted; with $M^+$, $R°$, X, X', X'' and Ar as defined above;

W represents a sigma σ bond, an oxygen or sulphur atom or a divalent radical i) —NR—, with R as defined above, or ii) methylene —$C(R_a)(R_b)$—, with $R_a$ and $R_b$, which are identical or different, representing a hydrogen atom or an aryl group, or else $R_a$ and $R_b$ form, together with the carbon atom which carries them, a spirocycloalkyl; preferably, W represents a sulphur atom or $R_a$ and $R_b$ together form a cyclohexyl;

it being understood that the formulae (II) and (II') comprise at least one sulphonate radical $R_1R_2R_3R_4N^+(O)_2S(O^-)$— or carboxylate radical $R_1R_2R_3R_4N^+(O)C(O^-)$— on one of the rings A, A', B, B' or C, with $R_1$, $R_2$, $R_3$ and $R_4$ as defined above; preferably, tetrabutylammonium sulphonate or carboxylate.

Mention may be made, as examples of dyes of formula (II), of the ammonium salts derived from: Acid Red 1, Acid Red 4, Acid Red 13, Acid Red 14, Acid Red 18, Acid Red 27, Acid Red 32, Acid Red 33, Acid Red 35, Acid Red 37, Acid Red 40, Acid Red 41, Acid Red 42, Acid Red 44, Acid Red 68, Acid Red 73, Acid Red 135, Acid Red 138, Acid Red 184, Food Red 1, Food Red 13, Acid Orange 6, Acid Orange 7, Acid Orange 10, Acid Orange 19, Acid Orange 20, Acid Orange 24, Acid Yellow 9, Acid Yellow 36, Acid Yellow 199, Food Yellow 3, Acid Violet 7, Acid Violet 14, Acid Blue 113, Acid Blue 117, Acid Black 1, Acid Brown 4, Acid Brown 20, Acid Black 26, Acid Black 52, Food Black 1 and Food Black 2;

and mention may be made, as examples of dyes of formula (II'), of the ammonium salts derived from: Acid Red 111, Acid Red 134 and Acid Yellow 38.

b) Pyrazolone Anionic Azo Dyes of Formulae (III) and (III'):

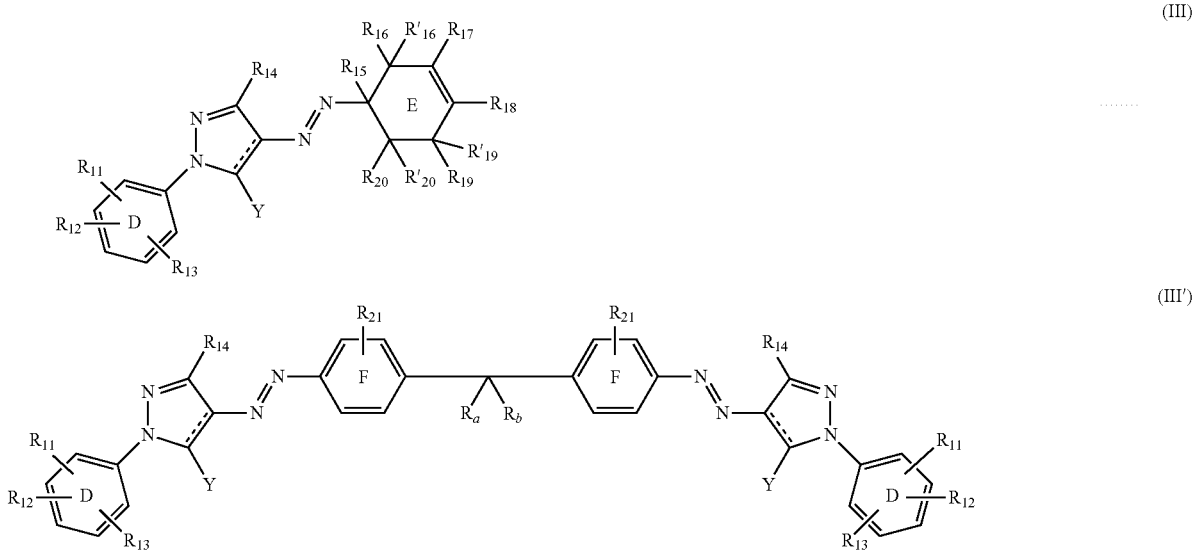

in which formulae (III) and (III'):
$R_{11}$, $R_{12}$ and $R_{11}$, which are identical or different, represent a hydrogen atom, a halogen atom, an alkyl group or an $M^+(O)_2S(O^-)$— group, with $M^+$ as defined above;
$R_{14}$ represents a hydrogen atom, an alkyl group or an $M^+C(O)O^-$— group, with $M^+$ as defined above;
$R_{15}$ represents a hydrogen atom;
$R_{16}$ represents an oxo group, in which case $R'_{16}$ is absent, or else $R_{15}$ with $R_{16}$ together form a double bond;
$R_{17}$ and $R_{18}$, which are identical or different, represent a hydrogen atom or a group chosen from:
$M^+(O)_2S(O^-)$—, with $M^+$ as defined above;
Ar—O—$S(O)_2$—, with Ar representing an optionally substituted aryl group; preferably, a phenyl optionally substituted by one or more alkyl groups;
$R_{19}$ and $R_{20}$, together form either a double bond or an optionally substituted benzo group D';
$R'_{16}$, $R'_{19}$, and $R'_{20}$, which are identical or different, represent a hydrogen atom, an alkyl group or a hydroxyl group;
$R_{21}$ represents a hydrogen atom, an alkyl group or an alkoxy group;
$R_a$ and $R_b$, which are identical or different, are as defined above; preferably, $R_a$ represents a hydrogen atom and $R_b$ represents an aryl group;
Y represents either a hydroxyl group or an oxo group;
----- represents a single bond when Y is an oxo group and represents a double bond when Y represents a hydroxyl group;
it being understood that the formulae (III) and (III') comprise at least one sulphonate group $R_1R_2R_3R_4N^+(O)_2S(O^-)$— on one of the rings D or E or the formulae (III) and (III') comprise at least one carboxylate group $R_1R_2R_3R_4N^+$(O)C(O$^-$)—, with $R_1$, $R_2$, $R_3$ and $R_4$ as defined above; preferably comprise at least one sulphonate group $R_1R_2R_3R_4N^+(O)_2S(O^-)$— on one of the rings D or E and more particularly tetrabutylammonium sulphonate.

Mention may be made, as examples of dyes of formula (III), of the ammonium salts derived from: Acid Red 195, Acid Yellow 23, Acid Yellow 27 and Acid Yellow 76, and mention may be made, as examples of dyes of formula (III'), of the ammonium salt derived from: Acid Yellow 17.

c) Anthraquinone Dyes of Formulae (IV) and (IV'):

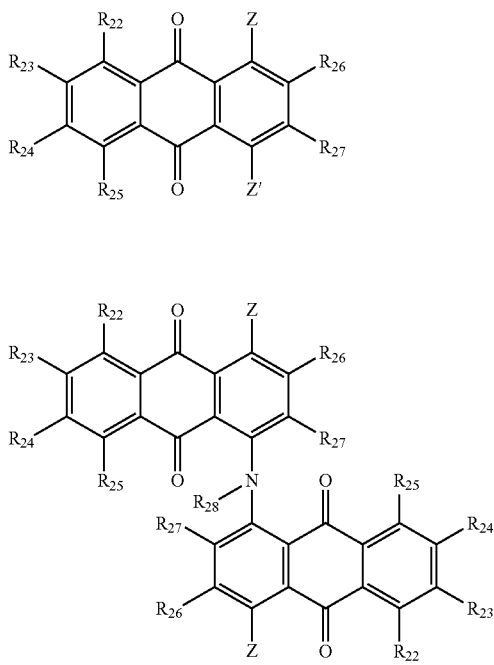

in which formulae (IV) and (IV'):
- $R_{22}$, $R_{23}$, $R_{24}$, $R_{25}$, $R_{26}$ and $R_{27}$, which are identical or different, represent a hydrogen atom, a halogen atom or a group chosen from:
  - alkyl;
  - hydroxyl, mercapto;
  - alkoxy, alkylthio;
  - optionally substituted aryloxy or arylthio, preferably substituted by one or more groups chosen from alkyl and $M^+(O)_2S(O^-)$—, with $M^+$ as defined above;
  - aryl(alkyl)amino optionally substituted by one or more groups chosen from alkyl and $M^+(O)_2S(O^-)$—, with $M^+$ as defined above;
  - (di)(alkyl)amino;
  - (di)(hydroxyalkyl)amino;
  - $M^+(O)_2S(O^-)$—, with $M^+$ as defined above;
- Z' represents a hydrogen atom or an $NR_{28}R_{29}$ group with $R_{28}$ and $R_{29}$, which are identical or different, representing a hydrogen atom or a group chosen from:
  - alkyl;
  - (poly)hydroxyalkyl, such as hydroxyethyl;
  - aryl optionally substituted by one or more groups, particularly i) alkyl, such as methyl, n-dodecyl or n-butyl; ii) $M^+(O)_2S(O^-)$—, with $M^+$ as defined above; iii) $R^\circ$—C(X)—X'—, $R^\circ$—X'—C(X)— or $R^\circ$—X'—C(X)—X"—, with $R^\circ$, X, X' and X" as defined above; preferably, $R^\circ$ represents an alkyl group;
  - cycloalkyl; in particular cyclohexyl;
- Z represents a group chosen from hydroxyl and $NR'_{28}R'_{29}$ with $R'_{28}$ and $R'_{29}$, which are identical or different, representing the same atoms or groups as $R_2$ and $R_{29}$ as defined above;

it being understood that the formulae (IV) and (IV') comprise at least one sulphonate group $R_1R_2R_3R_4N^+(O)_2S(O^-)$—, with $R_1$, $R_2$, $R_3$ and $R_4$ as defined above; preferably, tetrabutylammonium sulphonate.

d) Nitro Dyes of Formulae (V) and (V'):

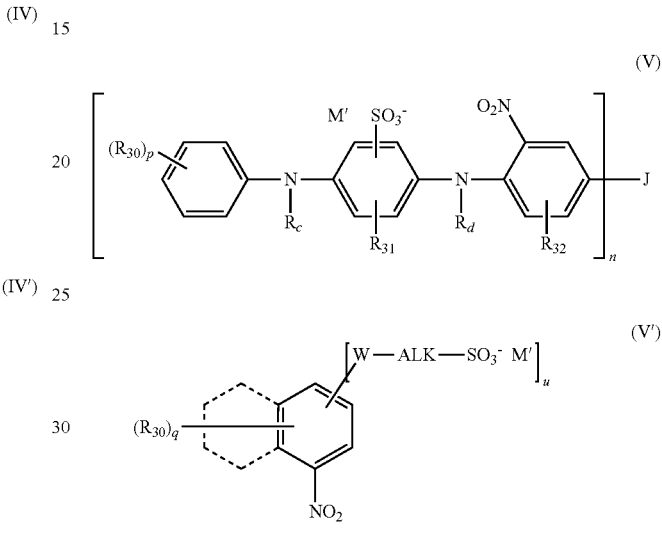

in which formulae (V) and (V'):
- $R_{30}$, $R_{31}$ and $R_{32}$, which are identical or different, represent a hydrogen atom, a halogen atom or a group chosen from:
  - alkyl;
  - alkoxy optionally substituted by one or more hydroxyl groups, or alkylthio optionally substituted by one or more hydroxyl groups;
  - hydroxyl, mercapto;
  - nitro, nitroso;
  - (poly)haloalkyl;
  - $R^\circ$—C(X)—X'—, $R^\circ$—X'—C(X)—, $R^\circ$—X'—C(X)—X"—, with $R^\circ$, X, X' and X" as defined above;
  - $M^+(O)_2S(O^-)$—, with $M^+$ as defined above;
  - $M^+$ (O)CO$^-$—, with $M^+$ as defined above;
  - (di)(alkyl)amino;
  - (di)(hydroxyalkyl)amino;
  - heterocycloalkyl, such as piperidino, piperazino or morpholino;
- in particular, $R_{30}$, $R_{31}$ and $R_{32}$ represent a hydrogen atom;
- $R_c$ and $R_d$, which are identical or different, represent a hydrogen atom or an alkyl group;
- W is as defined above; W represents in particular an —NH— group;
- ALK represents a linear or branched divalent $C_1$-$C_6$ alkylene group, in particular, ALK represents a —$CH_2CH_2$ group;
- n has a value of 1 or 2;
- p represents an integer between 1 and 5 inclusive;
- q represents an integer between 1 and 4 inclusive;
- u has a value of 0 or 1;

when n has a value of 1, J represents a nitro or nitroso group, in particular a nitro group;

when n has a value of 2, J represents an oxygen or sulphur atom or a divalent —S(O)$_m$— radical with m representing an integer which is 1 or 2; preferably, J represents an —SO$_2$— radical;

M' is as defined above for M$^+$;

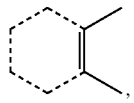

which is present or absent, represents a benzo group optionally substituted by one or more R$_{30}$ groups as defined above;

it being understood that the formulae (V) and (V') comprise at least one sulphonate group R$_1$R$_2$R$_3$R$_4$N$^+$(O)$_2$S(O$^-$)— or carboxylate group R$_1$R$_2$R$_3$R$_4$N$^+$(O)C(O$^-$)—, with R$_1$, R$_2$, R$_3$ and R$_4$ as defined above; preferably tetrabutylammonium sulphonate or carboxylate.

Mention may be made, as examples of dyes of formula (V), of the ammonium salts derived from: Acid Brown 13 and Acid Orange 3; mention may be made, as examples of dyes of formula (V'), of: Acid Yellow 1, sodium salt of 2,4-dinitro-1-naphthol-7-sulphonic acid, 2-pipendino-5-nitrobenzenesulphonic acid, 2-(4'-N,N(2''-hydroxyethyl)amino-2'-nitro)anilineethanesulphonic acid and 4-(β-hydroxyethylamino)-3-nitrobenzenesulphonic acid.

d) Triarylmethane Dyes of Formula (VI):

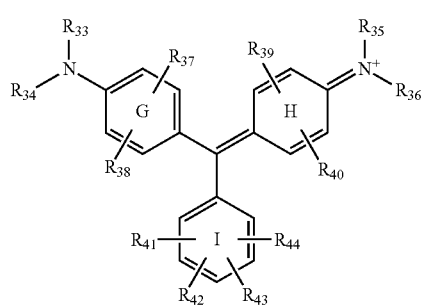

in which formula (VI):

R$_{33}$, R$_{34}$, R$_{35}$ and R$_{36}$, which are identical or different, represent a hydrogen atom or a group chosen from alkyl, optionally substituted aryl and optionally substituted arylalkyl, in particular an alkyl group and a benzyl group optionally substituted by an M$^+$(O)$_m$S(O$^-$)— group, with M$^+$ and m as defined above;

R$_{37}$, R$_{38}$, R$_{39}$, R$_{40}$, R$_{41}$, R$_{42}$, R$_{43}$ and R$_{44}$, which are identical or different, represent a hydrogen atom or a group chosen from:
alkyl;
alkoxy, alkylthio;
(di)(alkyl)amino;
hydroxyl, mercapto;
nitro, nitroso;
R°—C(X)—X'—, R°—X'—C(X)—, R°—X'—C(X)—X''—, with R° representing a hydrogen atom or an alkyl or aryl group and X, X' and X'', which are identical or different, representing an oxygen or sulphur atom or an NR group with R representing a hydrogen atom or an alkyl group;

M$^+$(O)$_2$S(O$^-$)—, with M$^+$ representing a hydrogen atom or a cationic counterion;

M$^+$(O)CO—, with M$^+$ as defined above;

or else two contiguous groups, R$_{41}$ with R$_{42}$ or R$_{42}$ with R$_{43}$ or R$_{43}$ with R$_{44}$, together form a fused benzo group: I'; with I' optionally substituted by one or more groups chosen from i) nitro; ii) nitroso; iii) M$^+$(O)$_2$S(O$^-$)—; iv) hydroxyl; v) mercapto; vi) (di)(alkyl)amino; vii) R°—C(X)—X'—; viii) R°—X'—C(X)—; ix) R°—X'—C(X)—X''—; with M$^+$, R°, X, X', X'' as defined above; in particular, R$_{37}$ to R$_{40}$ represent a hydrogen atom and R$_{41}$ to R$_{44}$, which are identical or different, represent a hydroxyl or M$^+$(O)$_2$S(O$^-$)— group; and, when R$_{43}$ with R$_{44}$ together form a benzo group, it is preferably substituted by an (O)$_2$S(O$^-$)— group;

it being understood that at least one of the rings G, H, I or I' comprises at least one sulphonate group R$_1$R$_2$R$_3$R$_4$N$^+$(O)$_2$S(O$^-$)— or carboxylate group R$_1$R$_2$R$_3$R$_4$N$^+$(O)C(O$^-$)—; preferably tetrabutylammonium sulphonate or carboxylate;

Mention may be made, as examples of dyes of formula (VI), of the ammonium salts derived from: Acid Blue 1, Acid Blue 3, Acid Blue 7, Acid Blue 9, Acid Violet 49 and Acid Green 50.

e) Xanthene-derived Dyes of Formula (VII):

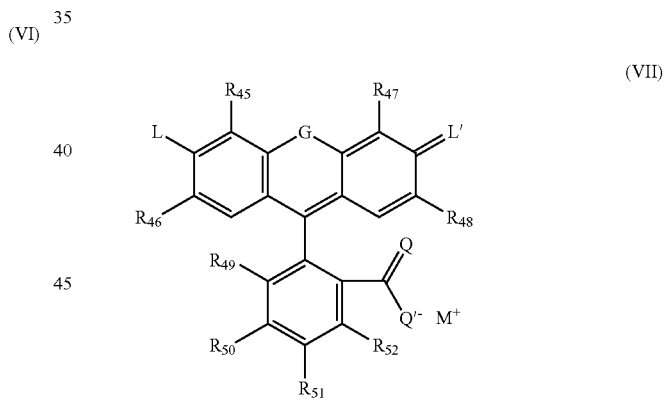

in which formula (VII):

R$_{45}$, R$_{46}$, R$_{47}$ and R$_{48}$, which are identical or different, represent a hydrogen atom or a halogen atom;

R$_{49}$, R$_{50}$, R$_{51}$ and R$_{52}$, which are identical or different, represent a hydrogen atom, a halogen atom or a group chosen from:
alkyl;
alkoxy, alkylthio;
hydroxyl, mercapto;
nitro, nitroso;
M$^+$(O)$_2$S(O$^-$)—, with M$^+$ representing a hydrogen atom or a cationic counterion;
M$^+$(O)CO—, with M$^+$ as defined above;
in particular R$_{53}$, R$_{54}$, R$_{55}$ and R$_{48}$ represent a hydrogen atom or a halogen atom;

G represents an oxygen or a sulphur atom or an $NR_e$ group, with $R_e$ as defined above; in particular, G represents an oxygen atom;

L represents an alkoxide $M^+O^-$—; a thioalkoxide $M^+S^-$ or an $NR_f$ group, with $R_f$ representing a hydrogen atom or an alkyl group and $M^+$ as defined above; $M^+$ is in particular sodium, potassium or $R_1R_2R_3R_4N^+$;

L' represents an oxygen or sulphur atom or an ammonium group: $N^+R_fR_g$, with $R_f$ and $R_g$, which are identical or different, representing a hydrogen atom, an alkyl group or an aryl group which is optionally substituted; L' represents in particular an oxygen atom or a phenylamino group optionally substituted by one or more alkyl or $M^+(O)_mS(O^-)$— groups, with m and $M^+$ as defined above;

Q and Q', which are identical or different, represent an oxygen or sulphur atom; in particular, Q and Q' represent an oxygen atom;

$M^+$ is as defined above;

it being understood that the formula (VII) comprises at least one sulphonate group $R_1R_2R_3R_4N^+(O)_2S(O^-)$— or carboxylate group $R_1R_2R_3R_4N^+(O)C(O^-)$—, with $R_1$, $R_2$, $R_3$ and $R_4$ as defined above; preferably tetrabutylammonium sulphonate or carboxylate.

Mention may be made, as examples of dyes of formula (VII), of the ammonium salts derived from: Acid Yellow 73, Acid Red 51, Acid Red 87, Acid Red 92, Acid Red 95 and Acid Violet 9.

f) Indole-derived Dyes of Formula (VIII):

(VIII)

in which formula (VIII):

$R_{53}$, $R_{54}$, $R_{55}$, $R_{56}$, $R_{57}$, $R_{58}$, $R_{59}$ and $R_{60}$, which are identical or different, represent a hydrogen atom or a group chosen from:

alkyl;
alkoxy, alkylthio;
hydroxyl, mercapto;
nitro, nitroso;
R—C(X)—X'—, R°—X'—C(X)—, R°—X'—C(X)—X"—, with R° representing a hydrogen atom or an alkyl or aryl group and X, X' and X", which are identical or different, representing an oxygen or sulphur atom or an NR group, with R representing a hydrogen atom or an alkyl group;
$M^+(O)_2S(O^-)$—, with $M^+$ as defined above;
$M^+(O)CO^-$—, with $M^+$ as defined above;
G represents an oxygen or sulphur atom or an $NR_e$ group, with $R_e$ as defined above; in particular, G represents an oxygen atom;
$R_i$ and $R_h$, which are identical or different, represent a hydrogen atom or an alkyl group;

it being understood that the formula (VIII) comprises at least one sulphonate group $R_1R_2R_3R_4N^+(O)_2S(O^-)$— or carboxylate group $R_1R_2R_3R_4N^+(O)C(O^-)$—, with $R_1$, $R_2$, $R_3$ and $R_4$ as defined above; preferably tetrabutylammonium sulphonate or carboxylate.

Mention may be made, as example of dyes of formula (VIII), of the ammonium salt derived from: Acid Blue 74.

g) Quinoline-derived Dyes of Formula (IX):

(IX)

in which formula (IX):

$R_{61}$ represents a hydrogen or halogen atom or an alkyl group;

$R_{62}$, $R_{63}$, and $R_{64}$, which are identical or different, represent a hydrogen atom or an $M^+(O)_2S(O^-)$— group, with $M^+$ as defined above;

or else $R_{61}$ with $R_{62}$ or $R_{61}$ with $R_{64}$ together form a benzo group optionally substituted by one or more $M^+(O)_2S(O^-)$— groups, with $M^+$ representing a hydrogen atom or a cationic counterion;

it being understood that the formula (IX) comprises at least one sulphonate group $R_1R_2R_3R_4N^+(O)_2S(O^-)$—, with $R_1$, $R_2$, $R_3$ and $R_4$ as defined above; preferably tetrabutylammonium sulphonate.

Mention may be made, as examples of dyes of formula (IX), of the ammonium salts derived from: Acid Yellow 2, Acid Yellow 3 and Acid Yellow 5.

More particularly, the dyes of formulae (II) to (VII) of use in the invention are chosen from the ammonium salts derived from:

| | |
|---|---|
| (C.I. 45380) | Acid Red 87 (VII) |
| (C.I. 10316) | 2,4-dinitro-1-naphthol-7-sulphonic acid (V') |
| (C.I. 10383) | Acid Orange 3 (V) |
| (C.I. 13015) | Acid Yellow 9/Food Yellow 2 (II) |
| (C.I. 14780) | Direct Red 45/Food Red 13 (II) |
| (C.I. 13711) | Acid Black 52 (II) |
| (C.I. 13065) | Acid Yellow 36 (II) |
| (C.I. 14700) | 1-hydroxy-2-(5'-sulphonato-2',4'-xylylazo)naphthalene-4-sulphonic acid/Food Red 1(II) |
| (C.I. 14720) | Acid Red 14/Food Red 3/Mordant Blue 79 (II) |
| (C.I. 14805) | 4-hydroxy-3-[(2-methoxy-5-nitrophenyl)diaza]-6-(phenylamino)naphthalene-2-sulphonic acid/Acid Brown 4 (II) |
| (C.I. 15510) | Acid Orange 7/Pigment Orange 17/Solvent Orange 49 (II) |
| (C.I. 15985) | Food Yellow 3/Pigment Yellow 104 (II) |
| (C.I. 16185) | Acid Red 27/Food Red 9 (II) |
| (C.I. 16230) | Acid Orange 10/Food Orange 4 (II) |
| (C.I. 16250) | Acid Red 44 (II) |
| (C.I. 17200) | Acid Red 33/Food Red 12 (II) |
| (C.I. 15685) | Acid Red 184 (II) |
| (C.I. 19125) | Acid Violet 3 (II) |
| (C.I. 18055) | 1-hydroxy-2-(4'-acetamidophenylazo)-8-acetamidonaphthalene-3,6-disulphonic acid/Acid Violet 7/Food Red 11(II) |
| (C.I. 18130) | Acid Red 135 (II) |
| (C.I. 19130) | Acid Yellow 27(III) |
| (C.I. 19140) | Acid Yellow 23/Food Yellow 4 (III) |
| (C.I. 20170) | 1,3-dihydroxy-2-(2",4"-dimethylphenylazo)-6-(4'-sulphonatophenylazo)-benzene/Acid Orange 24 (II) |
| (C.I. 20470) | 1-amino-2-(4'-nitrophenylazo)-7-phenylazo-8-hydroxynaphthalene-3,6-disulphonic acid/Acid Black 1 (II) |
| (C.I. 23266) | 4'-(4-((4-methylphenyl)sulphonyloxy)phenylazo)-2,2"-dimethyl-4-(1-hydroxy-3,6-disulphonato-2-naphthylazo)biphenyl/Acid Red 111 (II') |

-continued

| (C.I. 27755) | Food Black 2 (II) |
| (C.I. 28440) | 1-(4'-sulphonatophenylazo)-4-(8-acetylamino-1-hydroxy-3,5-disulphonato-2-naphthylazo)-6-sulphonatonaphthalene (tetrasodium salt)/Food Black 1 (II) |
| (C.I. 42090) | Acid Blue 9 (VI) |
| (C.I. 60730) | Acid Violet 43 (IV) |
| (C.I. 61570) | Acid Green 25 (IV) |
| (C.I. 62045) | 1-amino-4-cyclohexylamino-9,10-anthraquinone-2-sulphonic acid/Acid Blue 62 (IV) |
| (C.I. 62105) | Acid Blue 78 (IV) |
| (C.I. 14710) | 4-hydroxy-3-((2-methoxyphenyl)azo)-1-naphthalenesulphonic acid/Acid Red 4 (II) |
| | 2-piperidino-5-nitrobenzenesulphonic acid (V') |
| | 2-(4'-N,N(2''-hydroxyethyl)amino-2'-nitro)anilineethanesulphonic acid (V') |
| | 4-(β-hydroxyethylamino)-3-nitrobenzenesulphonic acid (V') |
| (C.I. 42640) | Acid Violet 49 (VI) |
| (C.I. 42080) | Acid Blue 7 (VI) |
| (C.I. 58005) | 1,2-dihydroxy-3-sulphoanthraquinone/Mordant Red 3 (IV) |
| (C.I. 62055) | 1-amino-9,10-dihydro-9,10-dioxo-4-(phenylamino)-2-anthracenesulphonic acid/Acid Blue 25 (IV) |
| (C.I. 14710) | 4-hydroxy-3-((2-methoxyphenyl)azo)-1-naphthalenesulphonic acid/Acid Red 4 (II) |

The majority of these dyes are described in particular in the Color Index published by The Society of Dyers and Colorists, P.O. Box 244, Perkin House, 82 Grattan Road, Bradford, Yorkshire, BD1 2JBN, England.

The anionic dyes according to the invention can be obtained by exchanges of cationic counterion with one or more ammoniums of $R_1R_2R_3R_4N^+$ type, with $R_1$, $R_2$, $R_3$ and $R_4$ as defined above.

The more particularly preferred anionic dyes for which the cationic counterions can be replaced are the dyes denoted in the Color Index under the code C.I. 58005 (monosodium salt of 1,2-dihydroxy-9,10-anthraquinone-3-sulphonic acid), C.I. 60730 (monosodium salt of 2-[(9,10-dihydro-4-hydroxy-9,10-dioxo-1-anthracenyl)amino]-5-methylbenzenesulphonic acid), C.I. 15510 (monosodium salt of 4-[(2-hydroxy-1-naphthyl)azo]benzenesulphonic acid), C.I. 15985 (disodium salt of 6-hydroxy-5-[(4-sulphophenyl)azo]-2-naphthalenesulphonic acid), C.I. 17200 (disodium salt of 5-amino-4-hydroxy-3-phenylazo-2,7-naphthalenedisulphonic acid), C.I. 20470 (disodium salt of 1-amino-2-(4'-nitrophenylazo)-7-phenylazo-8-hydroxy-3,6-naphthalenedisulphonic acid), C.I. 42090 (disodium salt of N-ethyl-N-[4-[[4-[ethyl[(3-sulphophenyl)methyl]amino]phenyl](2-sulphophenyl)methylene]-2,5-cyclohexadien-1-ylidene]-3-sulphobenzenemethanaminium hydroxide, internal salt) and C.I.61570 (disodium salt of 2,2'-[(9,10-dihydro-9,10-dioxo-1,4-anthracenediyl)diimino]bis[5-methylbenzenesulphonic acid].

Use may also be made of compounds corresponding to the mesomeric or tautomeric forms of the structures (II) to (IX).

More preferably, the anionic dyes of formula (I) according to the invention are chosen from those of formulae (II), (III) and (IV).

According to a specific embodiment of the invention, the dyes are chosen from (IIa), (IIIa) and (IVa) below:

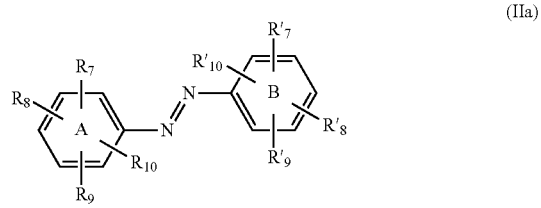

(IIa)

in which formula (IIa):

$R_7$, $R_8$, $R_9$, $R_{10}$, $R'_7$, $R'_8$, $R'_9$ and $R'_{10}$, which are identical or different, represent a hydrogen atom or a group chosen from:

hydroxyl;

nitro, nitroso;

(di)(alkyl)amino;

$M^+(O)_2S(O^-)$—, with $M^+$ representing a hydrogen atom, a cationic counterion or $R_1R_2R_3R_4N^+$ as defined above; and Ar—N=N— with Ar representing an optionally substituted aryl group; preferably a phenyl optionally substituted by one or more alkyl or $M^+(O)_2S(O^-)$— groups;

or else two contiguous groups $R_7$ with $R_8$ or $R_8$ with $R_9$ or $R_9$ with $R_{10}$ together form a fused benzo group A'; and $R'_7$ with $R'_8$ or $R'_8$ with $R'_9$ or $R'_9$ with $R'_{10}$ together form a fused benzo group B'; with A' and B' optionally substituted by one or more groups chosen from a) $M^+(O)_2S(O^-)$—; b) hydroxyl; c) Ar—N=N—; with $M^+$ and Ar as defined above;

it being understood that the formula (IIa) comprises at least one sulphonate radical $R_1R_2R_3R_4N^+(O)_2S(O^-)$— on one of the rings A, A', B, B', with $R_1$, $R_2$, $R_3$ and $R_4$ as defined above; preferably tetrabutylammonium sulphonate;

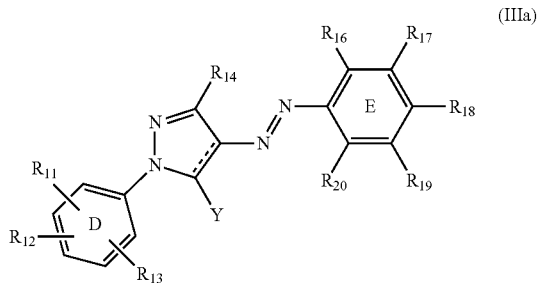

(IIIa)

in which formula (IIIa):

$R_{11}$, $R_{12}$ and $R_{13}$, which are identical or different, represent a hydrogen or halogen atom or an alkyl or $M^+(O)_2S(O^-)$— group, with $M^+$ as defined above;

$R_{14}$ represents a hydrogen atom, an alkyl group or an $M^+C(O^-)O^-$— group, with $M^+$ as defined above;

$R_{16}$, $R_{17}$, $R_{18}$, $R_{19}$, and $R_{20}$, which are identical or different, represent a hydrogen atom or an alkyl, hydroxyl or $M^+(O)_2S(O^-)$— group, with $M^+$ as defined above;

Y represents either a hydroxyl group or an oxo group;

----- represents a single bond when Y is an oxo group and represents a double bond when Y represents a hydroxyl group;

it being understood that the formula (IIIa) comprises at least one sulphonate group $R_1R_2R_3R_4N^+(O)_2S(O^-)$— on one of the rings D or E or carboxylate group $R_1R_2R_3R_4N^+(O)C(O^-)$—, with $R_1$, $R_2$, $R_3$ and $R_4$ as defined above; preferably tetrabutylammonium sulphonate;

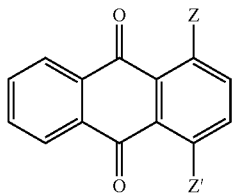

(IVa)

in which formula (IVa):

Z' represents an $NR_{28}R_{29}$ group, with $R_{28}$ representing a hydrogen atom or an alkyl group and $R_{29}$ representing an aryl group which is optionally substituted, in particular by one or more groups chosen from i) alkyl, such as methyl, and ii) $M^+(O)_2S(O^-)$—, with $M^+$ as defined above;

Z represents a group chosen from hydroxyl and $NR'_{28}R'_{29}$, with $R'_{28}$ and $R'_{29}$, which are identical or different, representing the same atoms or groups as $R_{28}$ and $R_{29}$ as defined above;

it being understood that the formula (IVa) comprises at least one sulphonate group $R_1R_2R_3R_4N^+(O)_2S(O^-)$—, with $R_1$, $R_2$, $R_3$ and $R_4$ as defined above; preferably tetrabutylammonium sulphonate.

Mention may be made, by way of examples, of the following anionic dyes:

| Anionic part "resulting" from commercial dye | Corresponding structure |
| --- | --- |
| Acid orange 7 | (belongs to the formulae (II) and (IIa)) |
| Acid black 1 | (belongs to the formulae (II) and (IIa)) |
| Acid red 18 | (belongs to the formulae (II) and (IIa)) |
| Acid yellow 23 | (belongs to the formulae (III) and (IIIa)) |

| Anionic part "resulting" from commercial dye | Corresponding structure |
|---|---|
| Acid violet 43 | 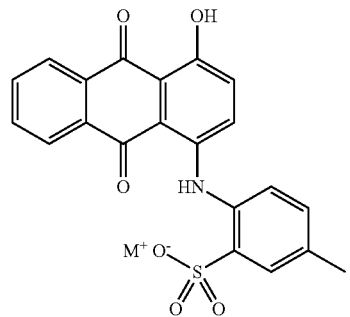<br>(belongs to the formulae (IV) and (IVa)) | with $M^+$, which are identical or different, as defined above, it being understood that at least one of the cationic counterions represents a cationic counterion $R_1R_2R_3R_4N^+$ as defined above; in particular, $M^+$ are identical and represent a tetrabutylammonium ($CH_3$—$CH_2$—$CH_2$—$CH_2)_4N^+$.

The dyes of formula (I) are derived from anionic dyes which are either commercially available or are accessible by syntheses employing conventional synthetic techniques known to a person skilled in the art. The "known" dyes comprise a cationic counterion, generally an inorganic counterion (alkali metal or alkaline earth metal cation), which is replaced by an organic ammonium counterion $R_1R_2R_3R_4N^+$ as defined above. This substitution of cationic counterions can be carried out by a conventional ion-exchange method, for example with an ion-exchange resin or with an ion-exchange column (ion exchange methodology, see for example, http://www.sigmaalddch.com/analytical-chromatography/sample-preparation/spe/ionexchange-methodology.html and "*Ion Exchange Material—Properties and Applications*", Andrei. A. Zagorodni, 1st Ed., 2007, Oxford, Elsevier BV; "Ion Exchange", H. Friedrich G, 1995, NY: MacGraw-Hill, chapt. 2.3, p. 12: Ion Exchange Resins, chapt. 3, p. 29: Cation Exchangers; chapt. 9, p. 421: Ion Exchange Column; *Ullmann's Encyclopedia of Industrial Chemistry*, "Ion Exchange" F. Dardel and Thomas V. Arden, Published Online: Apr. 15, 2008, DOI: 10.1002/14356007.a14_393.pub2; *Kirk-Othmer Encyclopedia of Chemical Technology*, "Ion Exchange" C. Dickert, Published Online: Apr. 12, 2000, DOI: 10.1002/0471238961.09151404090311.a01).

Another method consists in dissolving the known anionic dye in a water-immiscible organic solvent, such as halogenated organic solvents, for example dichloromethane, chloroform or methyl tetrachloride, or aromatic organic solvents, such as toluene or tetrahydrofuran (THF), and in adding thereto an aqueous solution comprising tetralkylammonium salts, such as tetraalkylammonium hydrogensulphate $R_1R_2R_3R_4N^+HO$—$S(O)_2O^-$ or tetraalkylammonium carboxylates $R_1R_2R_3R_4N^+R$—$C(O)O^-$, with R representing a hydrogen atom or a ($C_1$-$C_6$)alkyl group and $R_1R_2R_3R_4N^+$ being as defined above.

Depending on the amount of tetraalkylammonium salt added to the aqueous solution and on the number of sulphonate or carboxylate anionic group(s), it is possible to replace one or more cationic counterions. If, for example, all of the cationic counterions have to be replaced, then the choice is made to employ an aqueous solution saturated with tetraalkylammonium salt. The resulting mixture (aqueous solution+tetraalkylammonium salt+organic solvent+ "known" anionic dye) is subsequently left at ambient temperature with stirring for between 1 minute and one week, such as from 30 minutes to 48 hours, particularly one day and preferably between 2 and 4 hours. The organic phase is subsequently separated from the aqueous phase (by settling) and then optionally washed and separated again (by settling). The organic phase is optionally dried using a conventional dehydrating agent, such as alkali metal or alkaline earth metal sulphates, such as sodium sulphate, and then filtered. The starting organic solvent is subsequently evaporated, for example using a rotary evaporator of ROTAVAPOR® type.

II. Composition Comprising at Least One Anionic Dye of Formula (I)

Another subject-matter of the invention is a composition comprising, in a cosmetic medium, at least one anionic dye of formula (I) as defined above.

According to a particularly advantageous form of the invention, the cosmetic composition comprising one or more dyes of formula (I) does not comprise a chemical oxidizing agent.

The term "chemical oxidizing agent" is understood to mean any chemical or enzymatic oxidizing agent other than atmospheric oxygen.

The dyeing composition of use in the invention generally comprises an amount of anionic dye of formula (I) of between 0.001 and 50%, with respect to the total weight of the composition. Preferably, this amount is between 0.005 and 20% by weight and more preferably still between 0.01 and 5% by weight, with respect to the total weight of the composition.

The dyeing composition can moreover comprise additional direct dyes other than those of formula (I). These direct dyes are, for example, chosen from neutral, anionic or cationic nitrobenzene direct dyes, neutral, anionic or cationic azo direct dyes, tetraazapentamethine dyes, neutral, anionic or cationic quinone and in particular anthraquinone dyes, azine direct dyes, triarylmethane direct dyes, indoamine direct dyes and natural direct dyes.

Mention may be made, among natural direct dyes, of lawsone, juglone, alizarin, purpurin, carminic acid, kermesic acid, purpurogallin, protocatechualdehyde, indigo, isatin, curcumin, spinulosin or apigenidine. It is also possible to use extracts or decoctions comprising these natural dyes and in particular cataplasms or henna-based extracts.

The dyeing composition can comprise one or more oxidation bases and/or one or more couplers conventionally used for the dyeing of keratinous fibres.

Mention may be made, among oxidation bases, of paraphenylenediamines, bisphenylalkylenediamines, para-aminophenols, bis-para-aminophenols, ortho-aminophenols, heterocyclic bases and their addition salts.

Mention may in particular be made, among these couplers, of meta-phenylenediamines, meta-aminophenols, meta-diphenols, naphthalene couplers, heterocyclic couplers and their addition salts.

The coupler or couplers are each generally present in an amount of between 0.001 and 10% by weight of the total weight of the dyeing composition, preferably between 0.005 and 6% by weight.

The oxidation base or bases present in the dyeing composition are generally present each in an amount of between 0.001 and 10% by weight of the total weight of the dyeing composition, preferably between 0.005 and 6% by weight.

Generally, the addition salts of the oxidation bases and couplers which can be used in the context of the invention are chosen in particular from the addition salts with an acid, such as hydrochlorides, hydrobromides, sulphates, citrates, succinates, tartrates, lactates, tosylates, benzenesulphonates, phosphates and acetates, and the addition salts with a base, such as alkali metal hydroxides, for example sodium hydroxide or potassium hydroxide, ammonia, amines or alkanolamines.

The medium appropriate for the dyeing, also known as dyeing vehicle, is a cosmetic medium generally composed of water or of a mixture of water and of at least one organic solvent. Mention may be made, as organic solvent, for example, of lower $C_1$-$C_4$ alkanols, such as ethanol and isopropanol, polyols and polyol ethers, such as 2-butoxyethanol, propylene glycol, propylene glycol monomethyl ether, diethylene glycol monoethyl ether and diethylene glycol monomethyl ether, aromatic alcohols, such as benzyl alcohol or phenoxyethanol, and their mixtures.

The solvents, when they are present, are preferably present in proportions preferably of between 1 and 99% by weight approximately, with respect to the total weight of the dyeing composition, more preferably still between 5 and 95% by weight approximately.

The dyeing composition can also include various adjuvants conventionally used in hair-dyeing compositions, such as anionic, cationic, nonionic, amphoteric or zwitterionic surface-active agents or their mixtures, anionic, cationic, nonionic, amphoteric or zwitterionic polymers or their mixtures, inorganic or organic thickening agents, in particular anionic, cationic, nonionic and amphoteric polymeric associative thickeners, antioxidants, penetrating agents, sequestering agents, fragrances, buffers, dispersing agents, conditioning agents, such as, for example, volatile or non-volatile and modified or unmodified silicones, such as aminated silicones, film-forming agents, ceramides, preservatives, opacifying agents or conducting polymers.

The above adjuvants are generally present in an amount of, for each of them, between 0.01 and 20% by weight, with respect to the weight of the composition.

Of course, a person skilled in the art will take care to choose this or these optional additional compounds so that the advantageous properties intrinsically attached to the dyeing composition in accordance with the invention are not, or not substantially, detrimentally affected by the envisaged addition or additions.

The pH of the dyeing composition is generally between 3 and 14 approximately, preferably between 4 and 11 approximately and more particularly between 5 and 10. It can be adjusted to the desired value using acidifying or basifying agents commonly used in dyeing keratinous fibres or else using conventional buffer systems.

Mention may be made, among acidifying agents, by way of example, of inorganic or organic acids, such as: i) hydrochloric acid HCl, ii) hydrobromic acid HBr, iii) sulphuric acid $H_2SO_4$, iv) alkanesulphonic acids: Alk-S(O)$_2$OH, such as methanesulphonic acid and ethanesulphonic acid; v) arenesulphonic acids: Ar—S(O)$_2$OH, such as benzenesulphonic acid and toluenesulphonic acid; yl) citric acid; vii) succinic acid; viii) tartaric acid; ix) lactic acid; x) alkoxysulphinic acids: Alk-O—S(O)OH, such as methoxysulphinic acid and ethoxysulphinic acid; xi) aryloxysulphinic acids, such as tolyloxysulphinic acid and phenoxysulphinic acid; xii) phosphoric acid $H_3PO_4$; xiii) acetic acid $CH_3COOH$; xiv) triflic acid $CF_3SO_3H$; and xv) tetrafluoroboric acid $HBF_4$, more particularly hydrochloric acid, orthophosphoric acid, sulphuric acid, carboxylic acids, such as acetic acid, tartaric acid, citric acid or lactic acid, or sulphonic acids.

Mention may be made, among basifying agents, of inorganic or organic bases, more particularly ammonia, alkaline carbonates, alkanolamines, such as mono-, di- and triethanolamines and their derivatives, sodium hydroxide, potassium hydroxide and the compounds of following formula (γ):

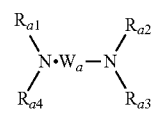

(γ)

in which formula (γ):
  $W_a$ is a ($C_1$-$C_{10}$)alkylene radical optionally substituted by a hydroxyl group or a $C_1$-$C_4$ alkyl radical and/or optionally substituted by one or more heteroatoms, such as O or N, preferably, W is a propylene;
  $R_{a1}$, $R_{a2}$, $R_{a3}$ and $R_{a4}$, which are identical or different, represent a hydrogen atom, a $C_1$-$C_4$ alkyl radical or a $C_1$-$C_4$ hydroxyalkyl radical.

The dyeing composition can be provided in various forms, such as in the form of a liquid, cream or gel or in any other form appropriate for carrying out dyeing of keratinous fibres and in particular of the hair.

III. Dyeing Method Starting from Anionic Dye of Formula (I)

Another subject-matter of the invention is a method for dyeing keratinous fibres which consists in applying, to the said fibres, a composition comprising at least one anionic dye of formula (I) as defined above.

The dyeing method according to the invention can also make it possible to optically lighten keratinous fibres, in particular dark keratinous fibres, such as keratinous fibres with a height of tone of less than or equal to 6 and in particular of less than or equal to 4, by employing a composition comprising at least one fluorescent anionic dye of formula (I), which are preferably dyes in the range of the orangey colours. Mention may be made in particular of xanthene-derived fluorescent dyes (VII) as defined above, in particular the ammonium derivatives of: Acid Yellow 73, Acid Red 51, Acid Red 87 and Acid Red 92. According to a particularly advantageous embodiment of the invention, the dyeing or optical lightening method does not involve any chemical oxidizing agent.

According to an alternative form of the dyeing method, once the composition comprising at least one anionic dye of formula (I) is applied to the keratinous fibres, the composition is left for a certain period of time and then the keratinous fibres are rinsed and/or superficially dried and then dried in air or with a hairdryer.

The duration of the treatment after application of the composition comprising at least one dye of formula (I) can be short, for example from 0.1 second to 1 hour, particularly between 5 minutes and 50 minutes and more particularly between 10 minutes and 45 minutes, and the leave-in time is preferably 30 minutes.

The examples which follow serve to illustrate the invention without, however, exhibiting a limiting nature.

The anionic dyes of the examples below were fully characterized by conventional spectroscopic and spectrometric methods.

PREPARATION EXAMPLE

General Preparation of the Dyes of the Invention: Counterion Exchange

A "known" anionic dye comprising the sodium counterion is suspended in dichloromethane. The water saturated with tetrabutylammonium hydrogensulphate is then added (equivalent volume) and then the mixture is stirred at ambient temperature for 3 hours. The organic phase is recovered and then washed several times with distilled water in order to remove the traces of starting dye. The organic phase is subsequently dried with sodium sulphate, filtered and then evaporated to dryness. Powders are obtained. The analyses are in accordance with the expected structures. The dyes synthesized are given below:

| Starting "known" dye | Structure of the dye obtained according to the invention |
|---|---|
| 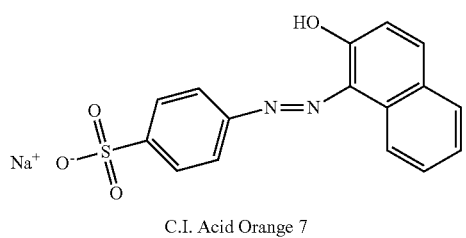 [SMILES: [Na+] ; O=S(=O)([O-])c1ccc(/N=N/c2c(O)ccc3ccccc23)cc1]<br>C.I. Acid Orange 7 | 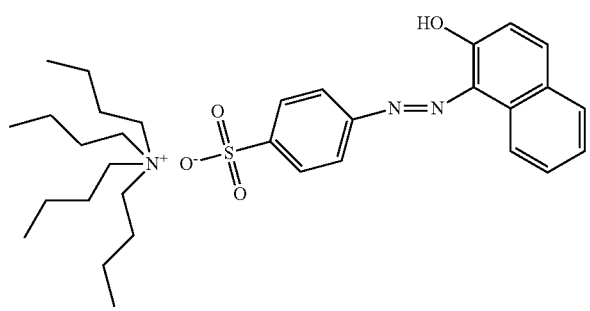<br>Dye 1 |
| 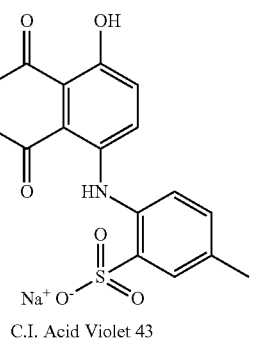<br>C.I. Acid Violet 43 | 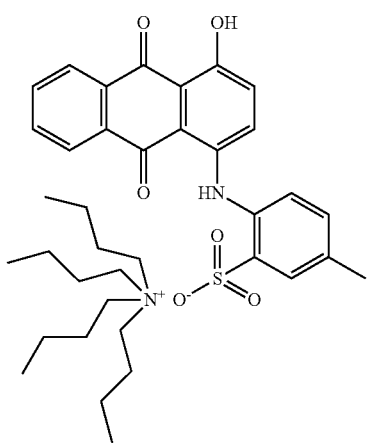<br>Dye 2 |

31
-continued
| Starting "known" dye | Structure of the dye obtained according to the invention |
|---|---|
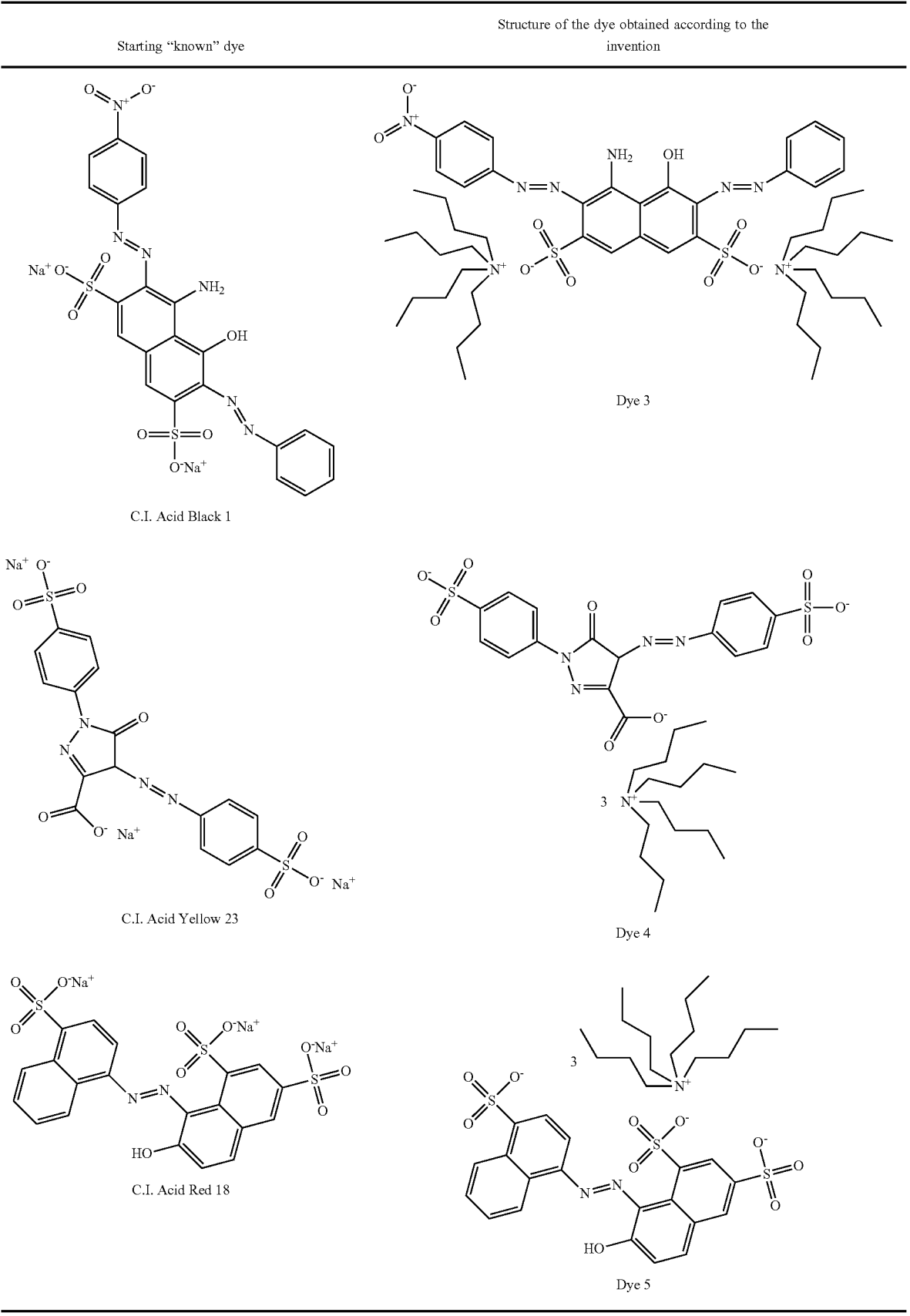
C.I. Acid Black 1 → Dye 3
C.I. Acid Yellow 23 → Dye 4
C.I. Acid Red 18 → Dye 5

Preparation of Dye 1

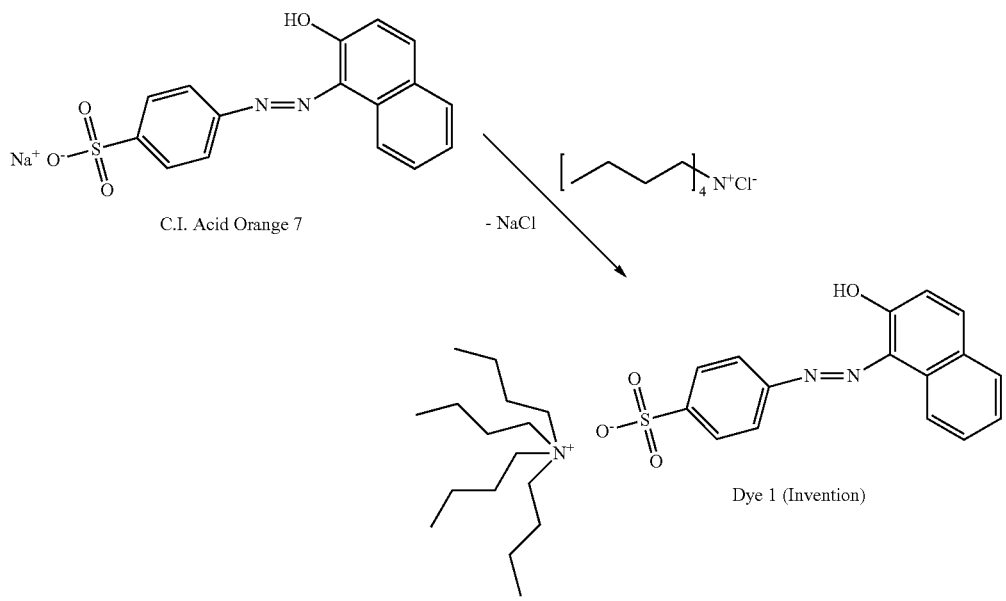

A mixture of C.I. Acid Orange 7 (17.5 g, 50 mmol), of tetrabutylammonium chloride (16.7 g, 60 mmol), of dichloromethane (200 ml) and of water (150 ml) is stirred for 2 h. The aqueous phase is recovered and washed twice with dichloromethane (2×200 ml) and then the three dichloromethane aliquots are combined, washed with water (3×200 ml) and then evaporated to dryness. An orange powder (23.1 g) is obtained. M.p.: 156-158° C.

DYEING EXAMPLE

Example 1

Dyeing Method

Two dyeing compositions were prepared according to the table below: a composition (A) comprising C.I. Acid Orange 7 (comparative) and a composition (B) comprising the dye 1 (invention):

| Compositions | (A), comparative | (B), invention |
|---|---|---|
| Benzoic acid | 0.5 g | 0.5 g |
| Ethanol | 15 g | 15 g |
| Benzyl alcohol | 5 g | 5 g |
| C.I. Acid Orange 7 (comparative) | $1 \times 10^{-4}$ mol | — |
| Dye 1 (invention) | — | $1 \times 10^{-4}$ mol |
| Water | q.s. for 100 g | q.s. for 100 g |

| Structure of the dye |
|---|
| C.I. Acid Orange 7 (comparative) 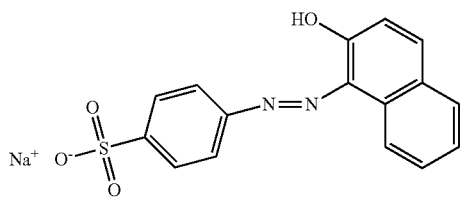 [SMILES: [Na+] ; O=S(=O)([O-])c1ccc(/N=N/c2c(O)ccc3ccccc23)cc1] |
| Dye 1 (invention) 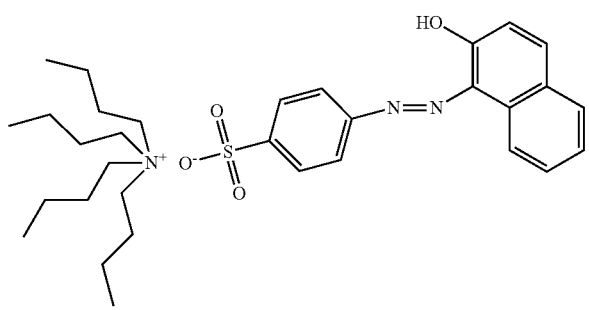 [SMILES: CCCC[N+](CCCC)(CCCC)CCCC ; O=S(=O)([O-])c1ccc(/N=N/c2c(O)ccc3ccccc23)cc1] |

Two locks weighing 1 g of hair (90% natural white hairs) originating from the same lock batch are subsequently steeped in 5 g of each dyeing composition (1 lock in the composition (A) and the other lock in the composition (B)). The locks are maintained in (A) and (B) at ambient temperature for 30 minutes. They are subsequently rinsed with water, shampooed once and then dried in air.

Results:

On conclusion of the dyeing, the colour of the locks is measured with a Minolta CM2600d spectrocolorimeter (specular components included, angle 10°, illuminant D65) in the C.I.E L*a*b* system. In this system, L* represents the intensity of the colour, a* indicates the green/red colour axis and b* indicates the blue/yellow colour axis.

ΔE represents the variation in colour between an "uncoloured" lock of hair and a coloured lock of hair and is determined from the following formula:

$$\Delta E = \sqrt{(L^* - L_o^*)^2 + (a^* - a_o^*)^2 + (b^* - b_o^*)^2}$$

in which L*, a* and b* represent the values measured on the coloured lock and $L_o^*$, $a_o^*$ and $b_o^*$ represent the values measured on the uncoloured lock.

The higher the value of ΔE, the more coloured is the lock.

C* represents the chromaticity in the C.I.E L*, a*, b* system, which is calculated according to the following equation:

$$C^* = \sqrt{a^{*2} + b^{*2}}$$

in which a* and b* are as defined above. The higher the value of C*, the greater the chromaticity of the colour.

The colorimetric results obtained are given in the tables below.

|  | L*(D65) | *(D65) | b*(D65) |
|---|---|---|---|
| Hairs (90% natural white hairs) | 54.25 | 1.64 | 11.08 |
| Composition A (comparative) | 50.15 | 10.77 | 18.78 |
| Composition B (invention) | 42.4 | 26.91 | 35.74 |

|  | C* | ΔE measured |
|---|---|---|
| Composition A (comparative) | 21.65 | 10.4 |
| Composition B (invention) | 44.74 | 27.5 |

It is apparent, from the above tables, that the colouring power of the dyes according to the invention is significantly greater than that of the comparative:

The variation in colour of the hair obtained before and after dyeing is significantly greater with the composition B, which comprises the dye 1 according to the invention, than that obtained with the comparative composition, which comprises the "known" anionic dye C.I. Acid Orange 7 (ΔE=27.5 vs 10.4).

The value of L* measured is in addition significantly lower for the colour of the hair obtained after treatment with the composition B than that obtained with the comparative composition (L=42.4 vs. 50.15). The colour of the hair thus appears visually much darker and consequently more powerful and more intense with the composition B according to the invention.

The colour obtained with the composition B according to the invention is significantly more chromatic than that obtained with the comparative composition (C*=44.74 vs. 21.65).

The invention claimed is:

1. A method for dyeing human keratinous fibers, said method comprising:
applying to the fibers a composition comprising at least one anionic dye of formula (I)

(I)

and optical isomers, geometric isomers, and solvates thereof, wherein in formula (I):

$R_1$, $R_2$, $R_3$ and $R_4$, which are identical, are chosen from i) linear ($C_1$-$C_6$)alkyls; and ii) linear ($C_2$-$C_6$)alkenyls;

it being possible for the alkyl or alkenyl group of the groups of i) and ii) to be interrupted by at least one identical or different heteroatoms chosen from oxygen, sulphur, and N(Rα), wherein Rα is chosen from hydrogen atoms and alkyl groups;

Col$^{(-)}$m represents the anionic part of the anionic dye comprising at least one sulphonate group and/or at least one carboxylate group, and wherein m is the anionic charge;

wherein m and n, which are identical or different, represent an integer ranging from 1 to 10;

wherein:

when the anionic part of the anionic dye comprises a sulphonate group or a carboxylate group, then m=n=1;

when the anionic part of the anionic dye comprises anionic groups other than a sulphonate or carboxylate group, the anionic part is combined with at least one cationic counterion, organic, inorganic or $R_1R_2R_3R_4N^+$, making it possible to achieve electrical neutrality of the formula (I); and the at least one anionic dye of formula (I) is chosen from the dyes of formulae (II), (II'), (lll), or (III'):

a) diaryl anionic azo dyes of formula (II) or (II'):

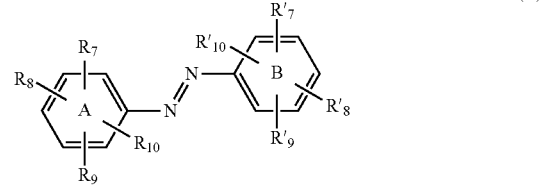

(II)

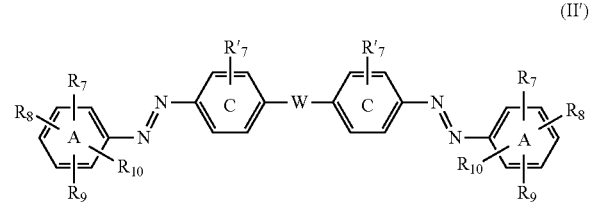

(II')

wherein in formulae (II) and (II'):

$R_7$, $R_8$, $R_9$, $R_{10}$, $R'_7$, $R'_8$, $R'_9$ and $R'_{10}$, which are identical or different, are chosen from a hydrogen atom or a group chosen from:

alkyl groups;

alkoxy groups or alkylthio groups;

hydroxyl groups or mercapto groups;

nitro groups or nitroso groups;

$R°—C(X)—X'—$, $R°—X'—C(X)—$, $R°—X'—C(X)—X"—$, wherein $R°$ is chosen from a hydrogen atom, alkyl groups, or aryl groups; and X, X' and X", which are identical or different, are chosen from oxygen atoms, sulphur atoms, or NR, wherein R is chosen from a hydrogen atom or an alkyl group;

$M^+(O)_2S(O^-)—$, wherein $M^+$ is chosen from hydrogen atoms, cationic counterions, or cationic counterions $R_1R_2R_3R_4N^+$;

$M^+(O)CO^-—$, wherein $M^+$ is chosen from hydrogen atoms, cationic counterions, or cationic counterions $R_1R_2R_3R_4N^+$;

$R"—S(O)_2—$, wherein $R"$ is chosen from hydrogen atoms, or an alkyl, aryl, (di)(alkyl)amino or aryl(alkyl)amino group;

$R'''—S(O)_2—X'—$, wherein $R'''$ is chosen from an alkyl group or an aryl group which is optionally substituted, and X' is chosen from oxygen atoms, sulphur atoms, or NR, wherein R is chosen from a hydrogen atom or an alkyl group;

(di)(alkyl)amino groups;

aryl(alkyl)amino, optionally substituted by at least one group chosen from i) nitro; ii) nitroso; iii) $M^+(O)_2S(O^-)—$ or iv) alkoxy groups, wherein $M^+$ is chosen from hydrogen atoms, cationic counterions, or cationic counterions $R_1R_2R_3R_4N^+$;

optionally substituted heteroaryl groups;

cycloalkyl groups;

Ar—N=N—, wherein Ar is an optionally substituted aryl group;

or else two contiguous groups, $R_7$ with $R_8$, $R_8$ with $R_9$, or $R_9$ with $R_{10}$, together form a fused benzo group A'; and $R'_7$ with $R'_8$ or $R'_8$ with $R'_9$ or $R'_9$ with $R'_{10}$ together form a fused benzo group B'; with A' and B' optionally substituted by one or more groups chosen from i) nitro; ii) nitroso; iii) $M^+(O)_2S(O^-)—$; iv) hydroxyl; v) mercapto; vi) (di)(alkyl)amino; vii) $R°—C(X)—X'—$; viii) $R°—X'—C(X)—$; ix) $R°—X'—C(X)—X"—$; x) Ar—N=N— and xi) aryl(alkyl)amino which is optionally substituted, wherein $M^+$ is chosen from hydrogen atoms, cationic counterions, or cationic counterions $R_1R_2R_3R_4N^+$;

W is chosen from a sigma σ bond, an oxygen or sulphur atom or a divalent radical i) —NR—, or ii) methylene —$C(R_a)(R_b)$—, wherein $R_a$ and $R_b$, which are identical or different, are chosen from a hydrogen atom or an aryl group, or else $R_a$ and $R_b$ form, together with the carbon atom which carries them, a spirocycloalkyl;

with the proviso that the formulae (II) and (II') comprise at least one sulphonate radical $R_1R_2R_3R_4N^+(O)_2S(O^-)—$ or carboxylate radical $R_1R_2R_3R_4N^+(O)C(O^-)—$ on one of the rings A, A', B, B' or C; or b) pyrazolone anionic azo dyes of formulae (III) or (III'):

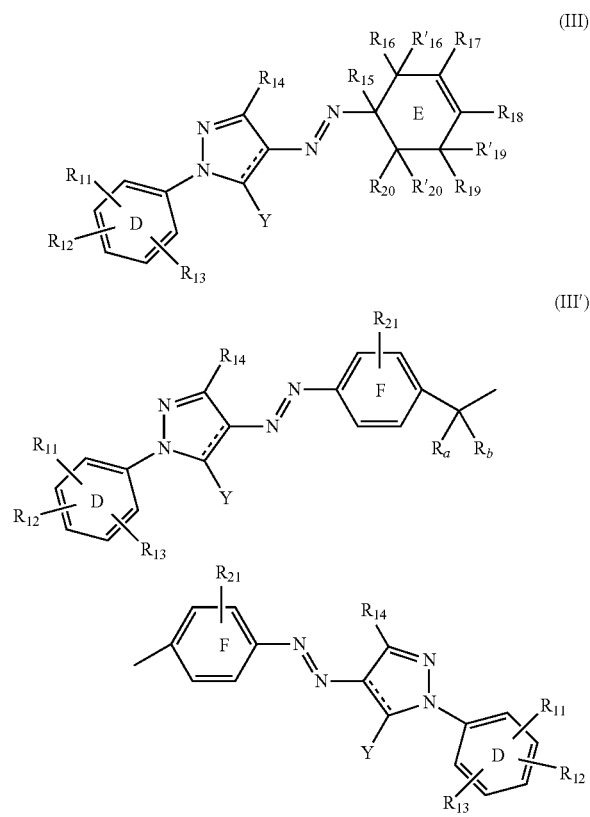

wherein in formulae (III) and (III'):

$R_{11}$, $R_{12}$ and $R_{13}$, which are identical or different, are chosen from a hydrogen atom, a halogen atom, an alkyl group or an $M^+(O)_2S(O^-)$– group, wherein $M^+$ is chosen from hydrogen atoms, cationic counterions, or cationic counterions $R_1R_2R_3R_4N^+$;

$R_{14}$ is chosen from a hydrogen atom, an alkyl group or an $M^+C(O)O^-$ group, wherein $M^+$ is chosen from hydrogen atoms, cationic counterions, or cationic counterions $R_1R_2R_3R_4N^+$;

$R_{15}$ represents a hydrogen atom;

$R_{16}$ represents an oxo group, in which case $R'_{16}$ is absent, or else $R_{15}$ with $R_{16}$ together form a double bond;

$R_{17}$ and $R_{18}$, which are identical or different, are chosen from a hydrogen atom or a group chosen from:

$M^+(O)_2S(O^-)—$, wherein $M^+$ is chosen from hydrogen atoms, cationic counterions, or cationic counterions $R_1R_2R_3R_4N^+$;

Ar—O—$S(O)_2—$, wherein Ar is an optionally substituted aryl group;

$R_{19}$ and $R_{20}$, together form either a double bond or an optionally substituted benzo group D';

$R'_{16}$, $R'_{19}$ and $R'_{20}$, which are identical or different, are chosen from a hydrogen atom, an alkyl group, or a hydroxyl group;

$R_{21}$ is chosen from a hydrogen atom, an alkyl group, or an alkoxy group;

$R_a$ and $R_b$, which are identical or different, are chosen from a hydrogen atom or an aryl group, or else $R_a$ and $R_b$ form, together with the carbon atom which carries them, a spirocycloalkyl;

Y is chosen from a hydroxyl group or an oxo group;
----- represents a single bond when Y is an oxo group and represents a double bond when Y represents a hydroxyl group;
with the proviso that the formulae (III) and (III') comprise at least one sulphonate group $R_1R_2R_3R_4N^+(O)_2S(O^-)$— on one of the rings D or E or the formulae (III) and (III') comprise at least one carboxylate group $R_1R_2R_3R_4N^+(O)C(O^-)$—.

2. The method according to claim 1, wherein $R_1$, $R_2$, $R_3$ and $R_4$ are identical.

3. The method according to claim 1, wherein $R_1$, $R_2$, $R_3$ and $R_4$ are independently chosen from linear $(C_1-C_6)$alkyl groups.

4. The method according to claim 1, wherein $R_1$, $R_2$, $R_3$ and $R_4$ are independently chosen from methyl, ethyl, propyl or butyl groups.

5. The method according to claim 1, wherein m is equal to n.

6. The method according to claim 1, in which m and n are independently chosen from 1, 2 or 3.

7. The method according to claim 1, wherein $Col^{(-)}_m$ comprises: at least one sulphonate group and at least one aryl or heteroaryl group, wherein the at least one sulphonate group is directly connected to an aryl or heteroaryl group; and optionally at least one anionic group $G^-$, wherein $G^-$, which is identical or different, represents an anionic group chosen from alkoxide $O^-$, thiolate $S^-$, carboxylate or thiocarboxylate $C(Q)Q'^-$, wherein Q and Q', which are identical or different, are chosen from oxygen or sulphur atoms.

8. The method according to claim 7, wherein $G^-$ is a carboxylate.

9. The method according to claim 1, wherein $Col^{(-)}_m$ comprises at least one carboxylate group and at least one aryl or heteroaryl group, wherein the at least one carboxylate group is directly connected to an aryl or heteroaryl group.

10. The method according to claim 1, wherein the anionic direct dye is chosen from acid azo dyes, each of these dyes having at least one sulphonate or carboxylate group having the cationic counterion $R_1R_2R_3R_4N^+$.

11. The method according to claim 1, wherein the at least one anionic dye of formula (I) is chosen from the diaryl anionic azo dyes of formula (II):

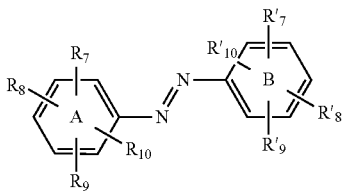

(II)

wherein:
$R_7$, $R_8$, $R_9$, $R_{10}$, $R'_7$, $R'_8$, $R'_9$ and $R'_{10}$, which are identical or different, are chosen from a hydrogen atom or a group chosen from:
alkyl groups;
alkoxy groups, alkylthio groups;
hydroxyl groups, mercapto groups;
nitro groups, nitroso groups;
$R°$—C(X)—X'—, $R°$—X'—C(X)—, $R°$—X'—C(X)—X"—, wherein $R°$ is chosen from hydrogen atoms alkyl groups, or aryl groups; and X, X' and X", which are identical or different, are chosen from oxygen atoms, sulphur atoms, or NR, wherein R is chosen from hydrogen atoms or alkyl groups;
$M^+(O)_2S(O^-)$—, wherein $M^+$ is chosen from hydrogen atoms, cationic counterions, or ammonium cationic counterions $R_1R_2R_3R_4N^+$;
$M^+(O)CO^-$—, wherein $M^+$ is chosen from hydrogen atoms, cationic counterions, or ammonium cationic counterions $R_1R_2R_3R_4N^+$;
$R"$—S(O)$_2$—, wherein $R"$ is chosen from hydrogen atoms or alkyl, aryl, (di)(alkyl)amino or aryl(alkyl)amino groups;
$R'''$—S(O)$_2$—X'—, wherein $R'''$ is chosen from alkyl groups or aryl groups, optionally substituted, and X' is chosen from oxygen atoms, sulphur atoms, or NR, wherein R is chosen from hydrogen atoms or alkyl groups;
(di)(alkyl)amino groups;
aryl(alkyl)amino groups, optionally substituted by at least one group chosen from nitro, nitroso, $M^+(O)_2S(O^-)$—, or alkoxy groups;
optionally substituted heteroaryl groups;
cycloalkyl groups;
Ar—N=N—, wherein Ar is an optionally substituted aryl group; or
two contiguous groups, $R_7$ with $R_8$, $R_8$ with $R_9$, $R_9$ with $R_{10}$, which together form a fused benzo group A'; and $R'_7$ with $R'_8$ or $R'_8$ with $R'_9$ or $R'_9$ with $R'_{10}$ together form a fused benzo group B'; wherein A' and B' are optionally substituted by at least one group chosen from nitro;
nitroso; $M^+(O)_2S(O^-)$—; hydroxyl; mercapto; (di)(alkyl)amino; $R°$—C(X)—X'—; $R°$—X'—C(X)—; $R°$—X'—C(X)—X"—; Ar—N=N—; or aryl(alkyl)amino which is optionally substituted;
wherein the diaryl anionic azo dye of formula (II) comprises at least one sulphonate radical $R_1R_2R_3R_4N^+(O)_2S(O^-)$— or carboxylate radical $R_1R_2R_3R_4N^+(O)C(O^-)$— on one of the rings A, A', B, or B'.

12. The method according to claim 1, wherein the at least one anionic dye of formula (I) is chosen from formulae (IIa):

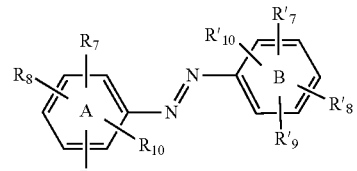

(IIa)

wherein in formula (IIa):
$R_7$, $R_8$, $R_9$, $R_{10}$, $R'_7$, $R'_8$, $R'_9$ and $R'_{10}$, which are identical or different, are chosen from hydrogen atoms or groups chosen from:
hydroxyl;
nitro, nitroso;
(di)(alkyl)amino;
$M^+(O)_2S(O^-)$—, wherein $M^+$ is chosen from hydrogen atoms, cationic counterions, or ammonium cationic counterions $R_1R_2R_3R_4N^+$; or
Ar—N=N—, wherein Ar is an optionally substituted aryl group;
two contiguous groups chosen from $R_7$ with $R_8$, $R_8$ with $R_9$, or $R_9$ with $R_{10}$, that together form a fused benzo group A'; and two contiguous groups chosen from R'$_7$ with R'$_8$, R'$_8$ with R'$_9$, or R'$_9$ with R'$_{10}$, that together form a fused benzo group B'; wherein A' and B' are optionally substituted by at least one group chosen from M$^+$(O)$_2$S(O$^-$)—; hydroxyl; or Ar—N=N—;
wherein the formula (IIa) comprises at least one sulphonate radical R$_1$R$_2$R$_3$R$_4$N$^+$(O)$_2$S(O$^-$)— or carboxylate radical R$_1$R$_2$R$_3$R$_4$N$^+$(O)C(O$^-$)— on one of the rings A, A', B, or B'.

13. The method according to claim 1, wherein the at least one anionic dye of formula (I) is chosen from:

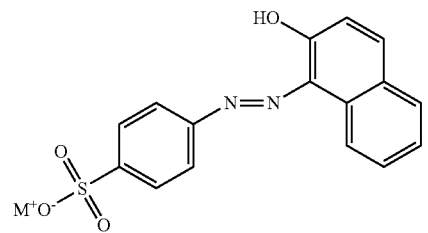

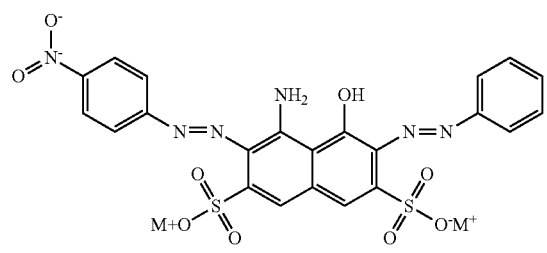

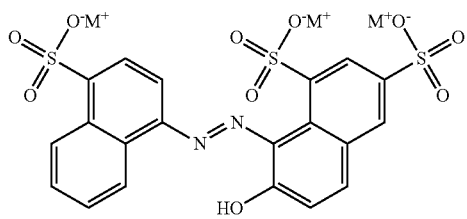

wherein M+, which is identical or different, is chosen from hydrogen atoms, cationic counterions, or ammonium cationic counterions R$_1$R$_2$R$_3$R$_4$N$^+$, wherein at least one of the cationic counterions is a cationic counterion R$_1$R$_2$R$_3$R$_4$N$^+$.

14. A method for dyeing and lightening dark human keratinous fibers having a height of tone of less than or equal to 6, comprising:
applying to the fibers, a composition comprising at least one fluorescent anionic dye of formula (I)

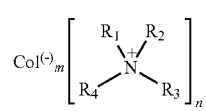

and optical isomers, geometric isomers, and solvates thereof, wherein in formula (I):
R$_1$, R$_2$, R$_3$ and R$_4$, which are identical, are chosen from i) linear (C$_1$-C$_6$)alkyls; and ii) linear (C$_2$-C$_6$)alkenyls;

it being possible for the alkyl or alkenyl group of the groups of i) and ii) to be interrupted by at least one identical or different heteroatoms chosen from oxygen, sulphur, and N(Rα), wherein Rα is chosen from hydrogen atoms and alkyl groups;
Col$^{(-)}{}_m$ represents the anionic part of the anionic dye comprising at least one sulphonate group and/or at least one carboxylate group, and wherein m is the anionic charges;
wherein m and n, which are identical or different, represent an integer ranging from 1 to 10;
wherein when the anionic part of the anionic dye comprises a sulphonate group or a carboxylate group, then m=n=1;
wherein when the anionic part of the anionic dye comprises anionic groups other than a sulphonate or carboxylate group, the anionic part is combined with at least one cationic counterion, organic, inorganic or R$_1$R$_2$R$_3$R$_4$N+, making it possible to achieve electrical neutrality of the formula (I); and
the at least one anionic dye of formula (I) is chosen from the dyes of formulae (II), (II'), (III), or (III'):

a) diaryl anionic azo dyes of formula (II) or (II'):

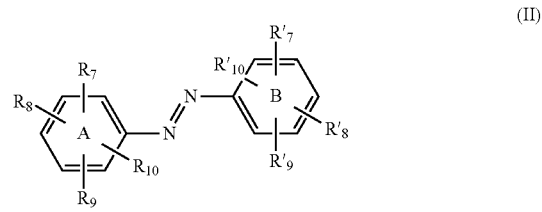

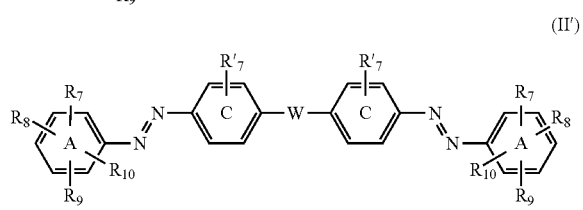

wherein in formulae (II) and (II'):
R$_7$, R$_8$, R$_9$, R$_{10}$, R'$_7$, R'$_8$, R'$_9$ and R'$_{10}$, which are identical or different, are chosen from a hydrogen atom or a group chosen from:
alkyl groups;
alkoxy groups or alkylthio groups;
hydroxyl groups or mercapto groups;
nitro groups or nitroso groups;
R°—C(X)—X'—, R°—X'—C(X)—, R°—X'—C(X)—X"—, wherein R° is chosen from a hydrogen atom, alkyl groups, or aryl groups; and X, X' and X", which are identical or different, are chosen from oxygen atoms, sulphur atoms, or NR, wherein R is chosen from a hydrogen atom or an alkyl group;
M$^+$(O)$_2$S(O$^-$)—, wherein M$^+$ is chosen from hydrogen atoms, cationic counterions, or cationic counterions R$_1$R$_2$R$_3$R$_4$N$^+$;
M$^+$(O)CO$^-$—, wherein M$^+$ is chosen from hydrogen atoms, cationic counterions, or cationic counterions R$_1$R$_2$R$_3$R$_4$N$^+$;
R"—S(O)$_2$—, wherein R" is chosen from hydrogen atoms, or an alkyl, aryl, (di)(alkyl)amino or aryl(alkyl)amino group;

R'''—S(O)$_2$—X'—, wherein R''' is chosen from an alkyl group or an aryl group which is optionally substituted, and X' is chosen from oxygen atoms, sulphur atoms, or NR, wherein R is chosen from a hydrogen atom or an alkyl group;
(di)(alkyl)amino groups;
aryl(alkyl)amino, optionally substituted by at least one group chosen from i) nitro; ii) nitroso; iii) M$^+$(O)$_2$S(O$^-$)— or iv) alkoxy groups, wherein M$^+$ is chosen from hydrogen atoms, cationic counterions, or cationic counterions R$_1$R$_2$R$_3$R$_4$N$^+$;
optionally substituted heteroaryl groups;
cycloalkyl groups;
Ar—N=N—, wherein Ar is an optionally substituted aryl group;
or else two contiguous groups, R$_7$ with R$_8$, R$_8$ with R$_9$, or R$_9$ with R$_{10}$, together form a fused benzo group A'; and R'$_7$ with R'$_8$ or R'$_8$ with R'$_9$ or R'$_9$ with R'$_{10}$ together form a fused benzo group B'; with A' and B' optionally substituted by one or more groups chosen from i) nitro; ii) nitroso; iii) M$^+$(O)$_2$S(O$^-$)—; iv) hydroxyl; v) mercapto; vi) (di)(alkyl)amino; vii) R°—C(X)—X'—; viii) R°—X'—C(X)—; ix) R°—X'—C(X)—X''—; x) Ar—N=N— and xi) aryl(alkyl)amino which is optionally substituted, wherein M$^+$ is chosen from hydrogen atoms, cationic counterions, or cationic counterions R$_1$R$_2$R$_3$R$_4$N$^+$;
W is chosen from a sigma σ bond, an oxygen or sulphur atom or a divalent radical i) —NR—, or ii) methylene —C(R$_a$)(R$_b$)—, wherein R$_a$ and R$_b$, which are identical or different, are chosen from a hydrogen atom or an aryl group, or else R$_a$ and R$_b$ form, together with the carbon atom which carries them, a spirocycloalkyl;
with the proviso that the formulae (II) and (II') comprise at least one sulphonate radical R$_1$R$_2$R$_3$R$_4$N$^+$(O)$_2$S(O$^-$)— or carboxylate radical R$_1$R$_2$R$_3$R$_4$N$^+$(O)C(O$^-$)— on one of the rings A, A', B, B' or C; or
b) pyrazolone anionic azo dyes of formulae (III) or (III'):

wherein in formulae (III) and (III'):
R$_{11}$, R$_{12}$ and R$_{13}$, which are identical or different, are chosen from a hydrogen atom, a halogen atom, an alkyl group or an M$^+$(O)$_2$S(O$^-$)— group, wherein M$^+$ is chosen from hydrogen atoms, cationic counterions, or cationic counterions R$_1$R$_2$R$_3$R$_4$N$^+$;
R$_{14}$ is chosen from a hydrogen atom, an alkyl group or an M$^+$C(O)O$^-$ group, wherein M$^+$ is chosen from hydrogen atoms, cationic counterions, or cationic counterions R$_1$R$_2$R$_3$R$_4$N$^+$;
R$_{15}$ represents a hydrogen atom;
R$_{16}$ represents an oxo group, in which case R'$_{16}$ is absent, or else R$_{15}$ with R$_{16}$ together form a double bond;
R$_{17}$ and R$_{18}$, which are identical or different, are chosen from a hydrogen atom or a group chosen from:
M$^+$(O)$_2$S(O$^-$)—, wherein M$^+$ is chosen from hydrogen atoms, cationic counterions, or cationic counterions R$_1$R$_2$R$_3$R$_4$N$^+$;
Ar—O—S(O)$_2$—, wherein Ar is an optionally substituted aryl group;
R$_{19}$ and R$_{20}$, together form either a double bond or an optionally substituted benzo group D';
R'$_{16}$, R'$_{19}$ and R'$_{20}$, which are identical or different, are chosen from a hydrogen atom, an alkyl group, or a hydroxyl group;
R$_{21}$ is chosen from a hydrogen atom, an alkyl group, or an alkoxy group;
R$_a$ and R$_b$, which are identical or different, are chosen from a hydrogen atom or an aryl group, or else R$_a$ and R$_b$ form, together with the carbon atom which carries them, a spirocycloalkyl;
Y is chosen from a hydroxyl group or an oxo group;
┅┅ represents a single bond when Y is an oxo group and represents a double bond when Y represents a hydroxyl group;
with the proviso that the formulae (III) and (III') comprise at least one sulphonate group R$_1$R$_2$R$_3$R$_4$N$^+$(O)$_2$S(O$^-$)— on one of the rings D or E or the formulae (III) and (III') comprise at least one carboxylate group R$_1$R$_2$R$_3$R$_4$N$^+$(O)C(O$^-$)—.

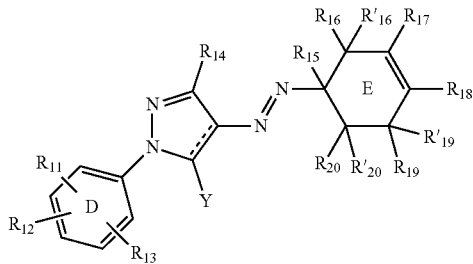

(III)

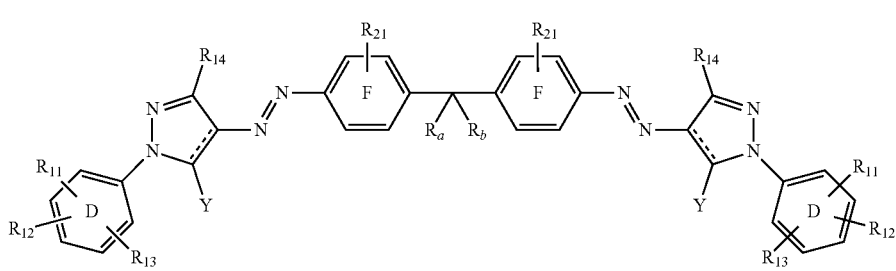

(III')

15. The method according to claim 14, wherein the keratinous fibers have a height of tone of less than or equal to 4.

16. The method according to claim 14, wherein the at least one fluorescent anionic dye is within the range of the orangey colors.

17. An anionic dye for dyeing human keratinous fibers of formula (I):

and optical isomers, geometric isomers, and solvates thereof, wherein in formula (I):

$R_1$, $R_2$, $R_3$ and $R_4$, which are identical, are chosen from i) linear ($C_1$-$C_6$)alkyls; and ii) linear ($C_2$-$C_6$)alkenyls;

it being possible for the alkyl or alkenyl group of the groups of i) and ii) to be interrupted by at least one identical or different heteroatoms chosen from oxygen, sulphur, and N(Rα), wherein Rα is chosen from hydrogen atoms and alkyl groups;

$Col^{(-)}{}_m$ represents the anionic part of the anionic dye comprising at least one sulphonate group and/or at least one carboxylate group and wherein m is the anionic charges;

wherein m and n, which are identical or different, represent an integer ranging from 1 to 10;

wherein:

when the anionic part of the anionic dye comprises a sulphonate group or a carboxylate group, then m=n=1;

when the anionic part of the anionic dye comprises anionic groups other than a sulphonate or carboxylate group, the anionic part is combined with at least one cationic counterion, organic, inorganic or $R_1R_2R_3R_4N^+$, making it possible to achieve electrical neutrality of the formula (I), the at least one anionic dye of formula (I) is chosen from the dyes of formulae (II), (II'), (III), or (III'):

a) diaryl anionic azo dyes of formula (II) or (II'):

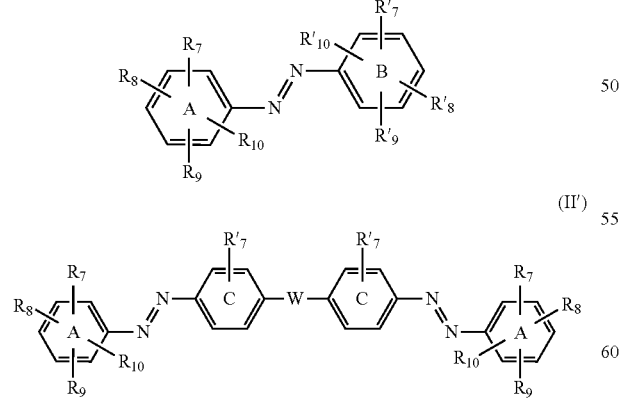

wherein in formulae (II) and (II'):

$R_7$, $R_8$, $R_9$, $R_{10}$, $R'_7$, $R'_8$, $R'_9$ and $R'_{10}$, which are identical or different, are chosen from a hydrogen atom or a group chosen from:

alkyl groups;

alkoxy groups or alkylthio groups;

hydroxyl groups or mercapto groups;

nitro groups or nitroso groups;

$R°$—C(X)—X'—, $R°$—X'—C(X)—, $R°$—X'—C(X)—X"—, wherein $R°$ is chosen from a hydrogen atom, alkyl groups, or aryl groups; and X, X' and X", which are identical or different, are chosen from oxygen atoms, sulphur atoms, or NR, wherein R is chosen from a hydrogen atom or an alkyl group;

$M^+(O)_2S(O^-)$—, wherein $M^+$ is chosen from hydrogen atoms, cationic counterions, or cationic counterions $R_1R_2R_3R_4N^+$;

$M^+(O)CO^-$—, wherein $M^+$ is chosen from hydrogen atoms, cationic counterions, or cationic counterions $R_1R_2R_3R_4N^+$;

$R"$—$S(O)_2$—, wherein $R"$ is chosen from hydrogen atoms, or an alkyl, aryl, (di)(alkyl)amino or aryl(alkyl)amino group;

$R'''$—$S(O)_2$—X'—, wherein $R'''$ is chosen from an alkyl group or an aryl group which is optionally substituted, and X' is chosen from oxygen atoms, sulphur atoms, or NR, wherein R is chosen from a hydrogen atom or an alkyl group;

(di)(alkyl)amino groups;

aryl(alkyl)amino, optionally substituted by at least one group chosen from i) nitro; ii) nitroso; iii) $M^+(O)_2S(O^-)$— or iv) alkoxy groups, wherein $M^+$ is chosen from hydrogen atoms, cationic counterions, or cationic counterions $R_1R_2R_3R_4N^+$;

optionally substituted heteroaryl groups;

cycloalkyl groups;

Ar—N=N—, wherein Ar is an optionally substituted aryl group;

or else two contiguous groups, $R_7$ with $R_8$, $R_8$ with $R_9$, or $R_9$ with $R_{10}$, together form a fused benzo group A'; and $R'_7$ with $R'_8$ or $R'_8$ with $R'_9$ or $R'_9$ with $R'_{10}$ together form a fused benzo group B'; with A' and B' optionally substituted by one or more groups chosen from i) nitro; ii) nitroso; iii) $M^+(O)_2S(O^-)$—; iv) hydroxyl; v) mercapto; vi) (di)(alkyl)amino; vii) $R°$—C(X)—X'—; viii) $R°$—X'—C(X)—; ix) $R°$—X'—C(X)—X"—; x) Ar—N=N— and xi) aryl(alkyl)amino which is optionally substituted, wherein $M^+$ is chosen from hydrogen atoms, cationic counterions, or cationic counterions $R_1R_2R_3R_4N^+$;

W is chosen from a sigma a bond, an oxygen or sulphur atom or a divalent radical i) —NR—, or ii) methylene —C($R_a$)($R_b$)—, wherein $R_a$ and $R_b$, which are identical or different, are chosen from a hydrogen atom or an aryl group, or else $R_a$ and $R_b$ form, together with the carbon atom which carries them, a spirocycloalkyl;

with the proviso that the formulae (II) and (II') comprise at least one sulphonate radical $R_1R_2R_3R_4N^+(O)_2S(O^-)$— or carboxylate radical $R_1R_2R_3R_4N^+(O)C(O^-)$— on one of the rings A, A', B, B' or C; or b) pyrazolone anionic azo dyes of formulae (III) or (III'):

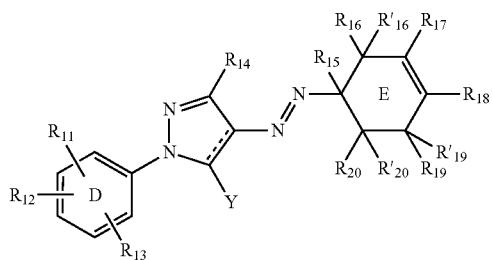

(III)

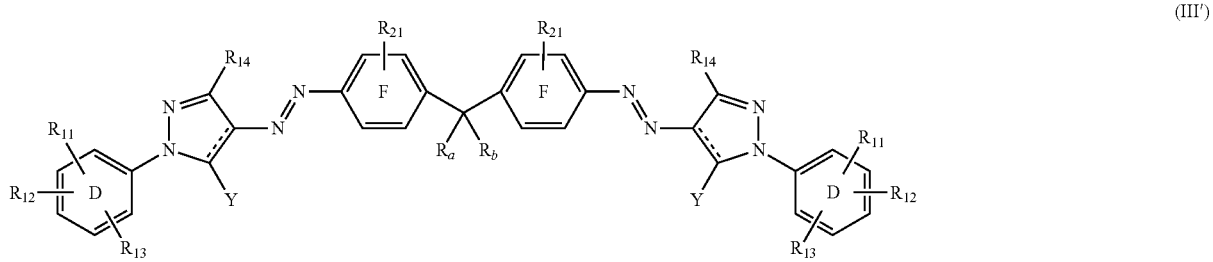

(III')

wherein in formulae (III) and (III'):
- $R_{11}$, $R_{12}$ and $R_{13}$, which are identical or different, are chosen from a hydrogen atom, a halogen atom, an alkyl group or an $M^+(O)_2S(O^-)$— group, wherein $M^+$ is chosen from hydrogen atoms, cationic counterions, or cationic counterions $R_1R_2R_3R_4N^+$;
- $R_{14}$ is chosen from a hydrogen atom, an alkyl group or an $M^+C(O)O^-$ group, wherein $M^+$ is chosen from hydrogen atoms, cationic counterions, or cationic counterions $R_1R_2R_3R_4N^+$;
- $R_{15}$ represents a hydrogen atom;
- $R_{16}$ represents an oxo group, in which case $R'_{16}$ is absent, or else $R_{15}$ with $R_{16}$ together form a double bond;
- $R_{17}$ and $R_{18}$, which are identical or different, are chosen from a hydrogen atom or a group chosen from:
  - $M^+(O)_2S(O^-)$—, wherein $M^+$ is chosen from hydrogen atoms, cationic counterions, or cationic counterions $R_1R_2R_3R_4N^+$;
  - Ar—O—S(O)$_2$—, wherein Ar is an optionally substituted aryl group;
- $R_{19}$ and $R_{20}$, together form either a double bond or an optionally substituted benzo group D';
- $R'_{16}$, $R'_{19}$ and $R'_{20}$, which are identical or different, are chosen from a hydrogen atom, an alkyl group, or a hydroxyl group;
- $R_{21}$ is chosen from a hydrogen atom, an alkyl group, or an alkoxy group;
- $R_a$ and $R_b$, which are identical or different, are chosen from a hydrogen atom or an aryl group, or else $R_a$ and $R_b$ form, together with the carbon atom which carries them, a spirocycloalkyl;
- Y is chosen from a hydroxyl group or an oxo group;
- ----- represents a single bond when Y is an oxo group and represents a double bond when Y represents a hydroxyl group;

with the proviso that the formulae (III) and (III') comprise at least one sulphonate group $R_1R_2R_3R_4N^+(O)_2S(O^-)$— on one of the rings D or E or the formulae (III) and (III') comprise at least one carboxylate group $R_1R_2R_3R_4N^+(O)C(O^-)$—;

wherein the anionic dye of formula (I) is different from the dyes of formulae (a) to (u):

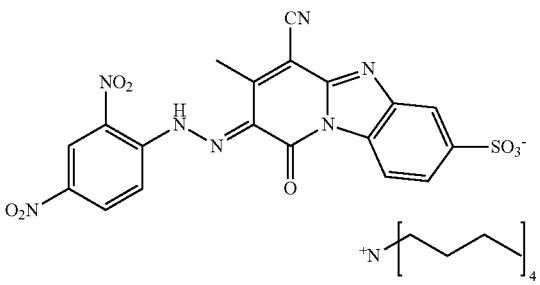

(a)

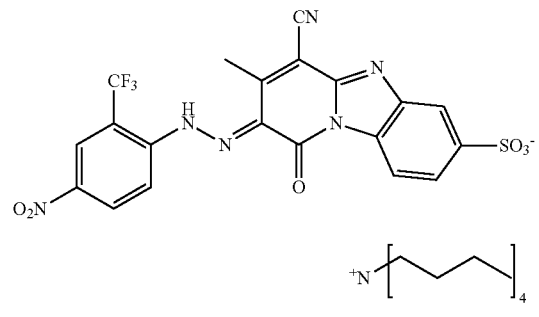

(b)

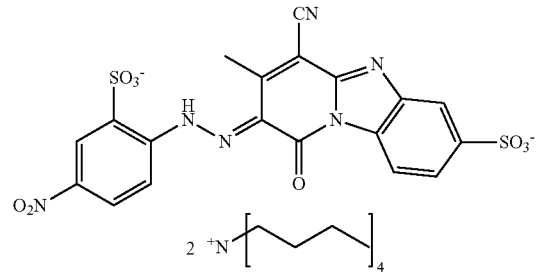

(c)

-continued (d)
(e)
(f)
(g)
(h)
(i)
(j)
(k)
(l)
(m)

-continued (n)
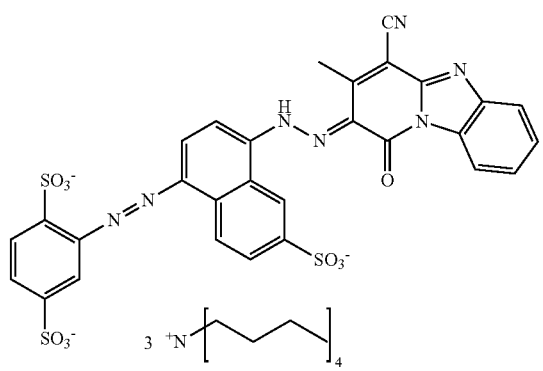

(o)
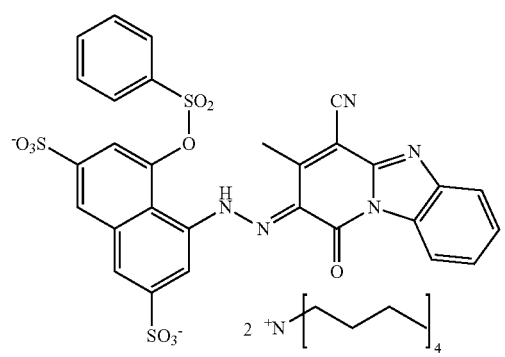

(p)
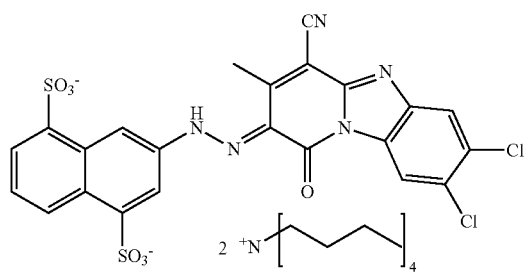

(q)
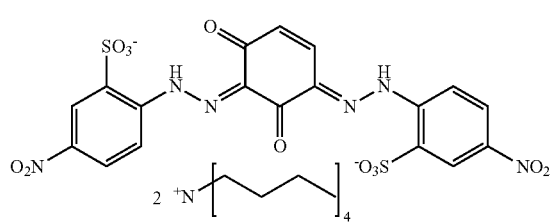

(r)
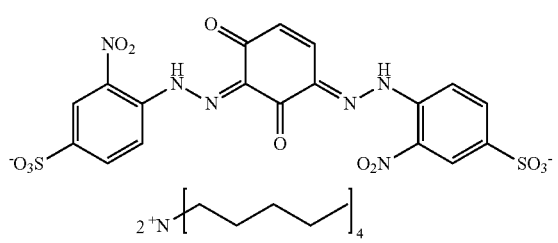

-continued (s)
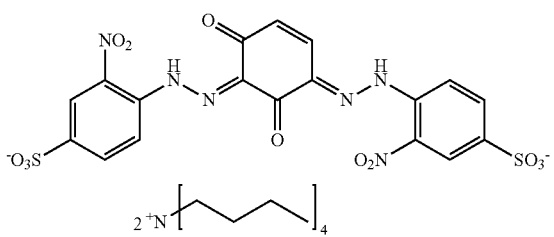

(t)
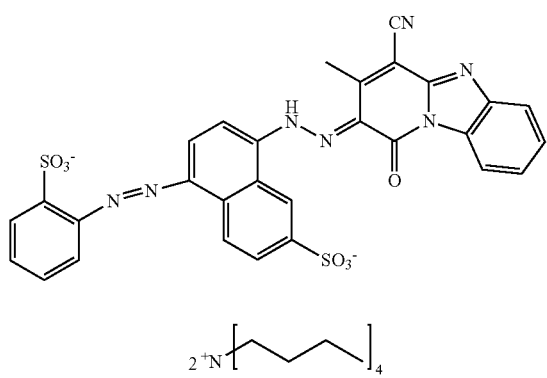

(u)
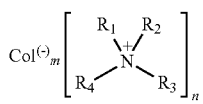

18. A dyeing composition for dyeing human keratinous fibers, said composition comprising at least one anionic dye of formula (I):

$$\text{Col}^{(-)}{}_m \left[ \begin{array}{c} R_1 \diagdown {}^+ \diagup R_2 \\ N \\ R_4 \diagup \diagdown R_3 \end{array} \right]_n \quad (I)$$

and optical isomers, geometric isomers, and solvates thereof, wherein in formula (I):

$R_1$, $R_2$, $R_3$ and $R_4$, which are identical, are chosen from i) linear ($C_1$-$C_6$)alkyls; and ii) linear ($C_2$-$C_6$)alkenyls;
it being possible for the alkyl or alkenyl group of the groups of i) and ii) to be interrupted by at least one identical or different heteroatoms chosen from oxygen, sulphur, and $N(R\alpha)$, wherein $R\alpha$ is chosen from hydrogen atoms and alkyl groups;
$\text{Col}^{(-)}{}_m$ represents the anionic part of the anionic dye comprising at least one sulphonate group and/or at least one carboxylate group and wherein m is the anionic charges;

wherein m and n, which are identical or different, represent an integer ranging from 1 to 10;
wherein:
when the anionic part of the anionic dye comprises a sulphonate group or a carboxylate group, then m=n=1;
when the anionic part of the anionic dye comprises anionic groups other than a sulphonate or carboxylate group, the anionic part is combined with at least one cationic counterion, organic, inorganic or $R_1R_2R_3R_4N^+$, making it possible to achieve electrical neutrality of the formula (I),
the at least one anionic dye of formula (I) is chosen from the dyes of formulae (II), (II'), (III), or (III'):
a) diaryl anionic azo dyes of formula (II) or (II'):

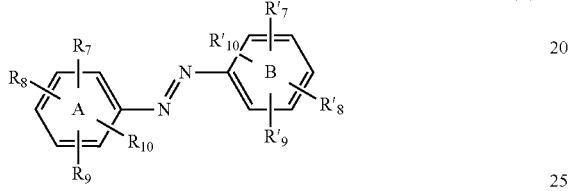

(II)

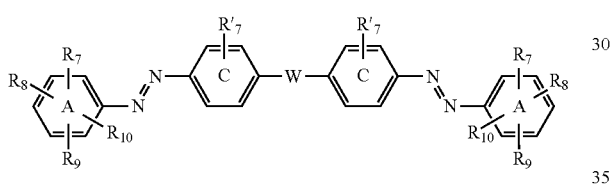

(II')

wherein in formulae (II) and (II'):
$R_7$, $R_8$, $R_9$, $R_{10}$, $R'_7$, $R'_8$, $R'_9$ and $R'_{10}$, which are identical or different, are chosen from a hydrogen atom or a group chosen from:
alkyl groups;
alkoxy groups or alkylthio groups;
hydroxyl groups or mercapto groups;
nitro groups or nitroso groups;
$R°$—C(X)—X'—, $R°$—X'—C(X)—, $R°$—X'—C(X)—X"—, wherein $R°$ is chosen from a hydrogen atom, alkyl groups, or aryl groups; and X, X' and X", which are identical or different, are chosen from oxygen atoms, sulphur atoms, or NR, wherein R is chosen from a hydrogen atom or an alkyl group;

$M^+(O)_2S(O^-)$—, wherein $M^+$ is chosen from hydrogen atoms, cationic counterions, or cationic counterions $R_1R_2R_3R_4N^+$;
$M^+(O)CO^-$—, wherein $M^+$ is chosen from hydrogen atoms, cationic counterions, or cationic counterions $R_1R_2R_3R_4N^+$;
R"—$S(O)_2$—, wherein R" is chosen from hydrogen atoms, or an alkyl, aryl, (di)(alkyl)amino or aryl(alkyl)amino group;
R'''—$S(O)_2$—X'—, wherein R''' is chosen from an alkyl group or an aryl group which is optionally substituted, and X' is chosen from oxygen atoms, sulphur atoms, or NR, wherein R is chosen from a hydrogen atom or an alkyl group;
(di)(alkyl)amino groups;
aryl(alkyl)amino, optionally substituted by at least one group chosen from i) nitro; ii) nitroso; iii) $M^+(O)_2S(O^-)$— or iv) alkoxy groups, wherein $M^+$ is chosen from hydrogen atoms, cationic counterions, or cationic counterions $R_1R_2R_3R_4N^+$;
optionally substituted heteroaryl groups;
cycloalkyl groups;
Ar—N=N—, wherein Ar is an optionally substituted aryl group;
or else two contiguous groups, $R_7$ with $R_8$, $R_8$ with $R_9$, or $R_9$ with $R_{10}$, together form a fused benzo group A'; and $R'_7$ with $R'_8$ or $R'_8$ with $R'_9$ or $R'_9$ with $R'_{10}$ together form a fused benzo group B'; with A' and B' optionally substituted by one or more groups chosen from i) nitro; ii) nitroso; iii) $M^+(O)_2S(O^-)$—; iv) hydroxyl; v) mercapto; vi) (di)(alkyl)amino; vii) $R°$—C(X)—X'—; viii) $R°$—X'—C(X)—; ix) $R°$—X'—C(X)—X"—; x) Ar—N=N— and xi) aryl(alkyl)amino which is optionally substituted, wherein $M^+$ is chosen from hydrogen atoms, cationic counterions, or cationic counterions $R_1R_2R_3R_4N^+$;
W is chosen from a sigma σ bond, an oxygen or sulphur atom or a divalent radical i) —NR—, or ii) methylene —$C(R_a)(R_b)$—, wherein $R_a$ and $R_b$, which are identical or different, are chosen from a hydrogen atom or an aryl group, or else $R_a$ and $R_b$ form, together with the carbon atom which carries them, a spirocycloalkyl;
with the proviso that the formulae (II) and (II') comprise at least one sulphonate radical $R_1R_2R_3R_4N^+(O)_2S(O^-)$— or carboxylate radical $R_1R_2R_3R_4N^+(O)C(O^-)$— on one of the rings A, A', B, B' or C; or
b) pyrazolone anionic azo dyes of formulae (III) or (III'):

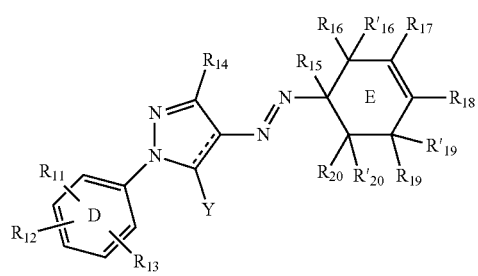

(III)

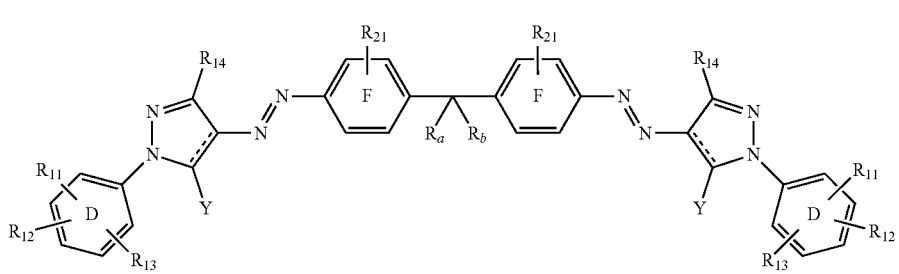

(III')

wherein in formulae (III) and (III'):

$R_{11}$, $R_{12}$ and $R_{13}$, which are identical or different, are chosen from a hydrogen atom, a halogen atom, an alkyl group or an $M^+(O)_2S(O^-)$— group, wherein $M^+$ is chosen from hydrogen atoms, cationic counterions, or cationic counterions $R_1R_2R_3R_4N^+$;

$R_{14}$ is chosen from a hydrogen atom, an alkyl group or an $M^+C(O)O^-$ group, wherein $M^+$ is chosen from hydrogen atoms, cationic counterions, or cationic counterions $R_1R_2R_3R_4N^+$;

$R_{15}$ represents a hydrogen atom;

$R_{16}$ represents an oxo group, in which case $R'_{16}$ is absent, or else $R_{15}$ with $R_{16}$ together form a double bond;

$R_{17}$ and $R_{18}$, which are identical or different, are chosen from a hydrogen atom or a group chosen from:
- $M^+(O)_2S(O^-)$—, wherein $M^+$ is chosen from hydrogen atoms, cationic counterions, or cationic counterions $R_1R_2R_3R_4N^+$;
- Ar—O—S(O)$_2$—, wherein Ar is an optionally substituted aryl group;

$R_{19}$ and $R_{20}$, together form either a double bond or an optionally substituted benzo group D';

$R'_{16}$, $R'_{19}$ and $R'_{20}$, which are identical or different, are chosen from a hydrogen atom, an alkyl group, or a hydroxyl group;

$R_{21}$ is chosen from a hydrogen atom, an alkyl group, or an alkoxy group;

$R_a$ and $R_b$, which are identical or different, are chosen from a hydrogen atom or an aryl group, or else $R_a$ and $R_b$ form, together with the carbon atom which carries them, a spirocycloalkyl;

Y is chosen from a hydroxyl group or an oxo group;

- - - - represents a single bond when Y is an oxo group and represents a double bond when Y represents a hydroxyl group;

with the proviso that the formulae (III) and (III') comprise at least one sulphonate group $R_1R_2R_3R_4N^+(O)_2S(O^-)$— on one of the rings D or E or the formulae (III) and (III') comprise at least one carboxylate group $R_1R_2R_3R_4N^+(O)C(O^-)$—;

the anionic dye of formula (I) is different from the dyes of formulae (a) to (u):

(a)

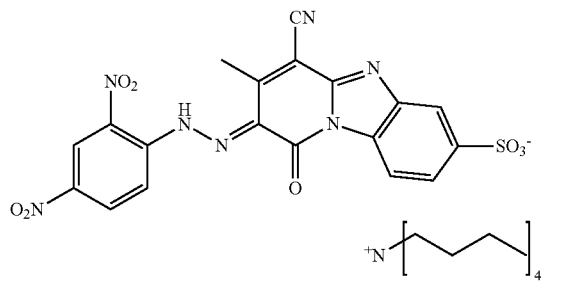

(b)

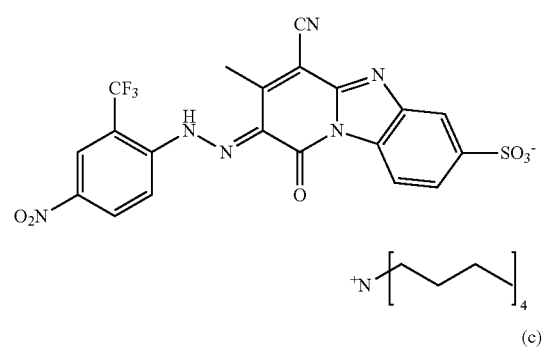

(c)

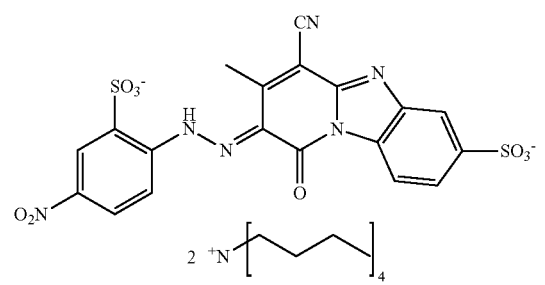

(d)

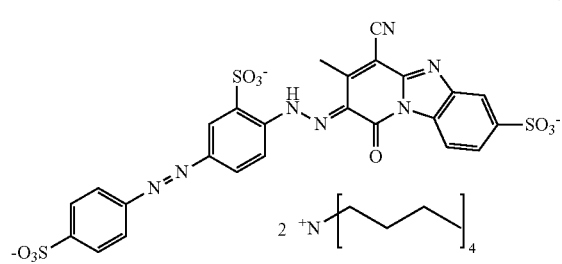

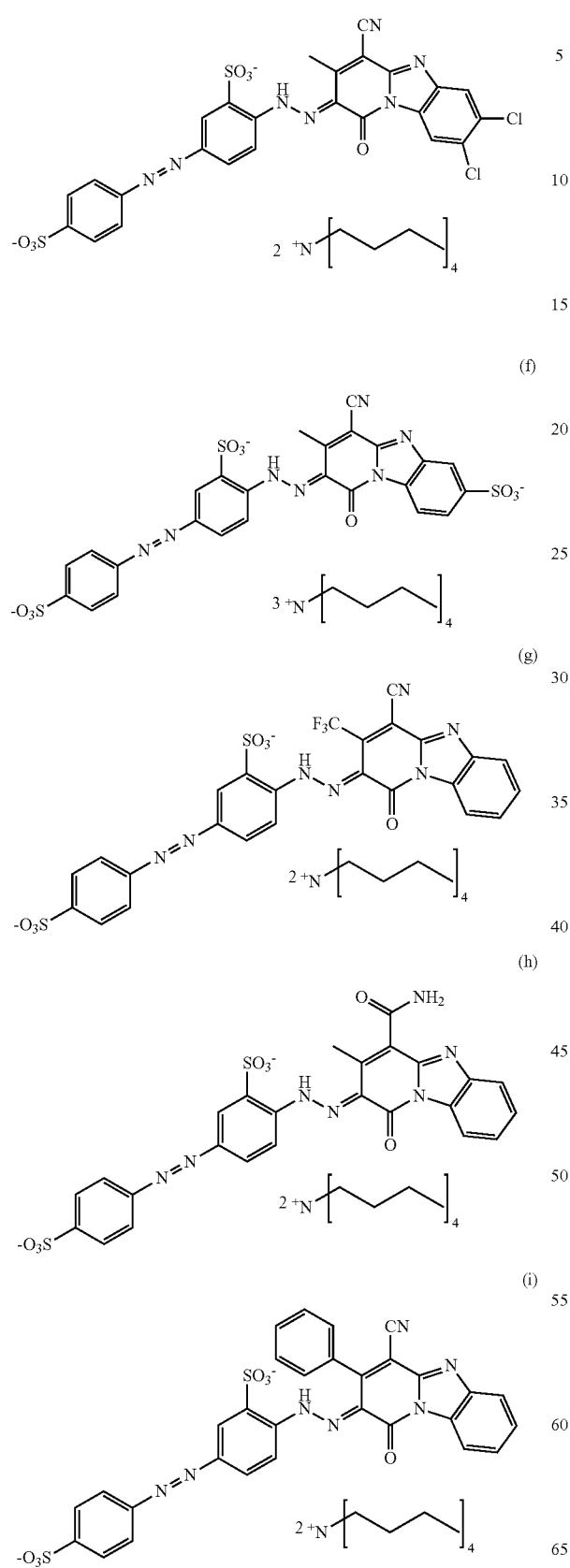
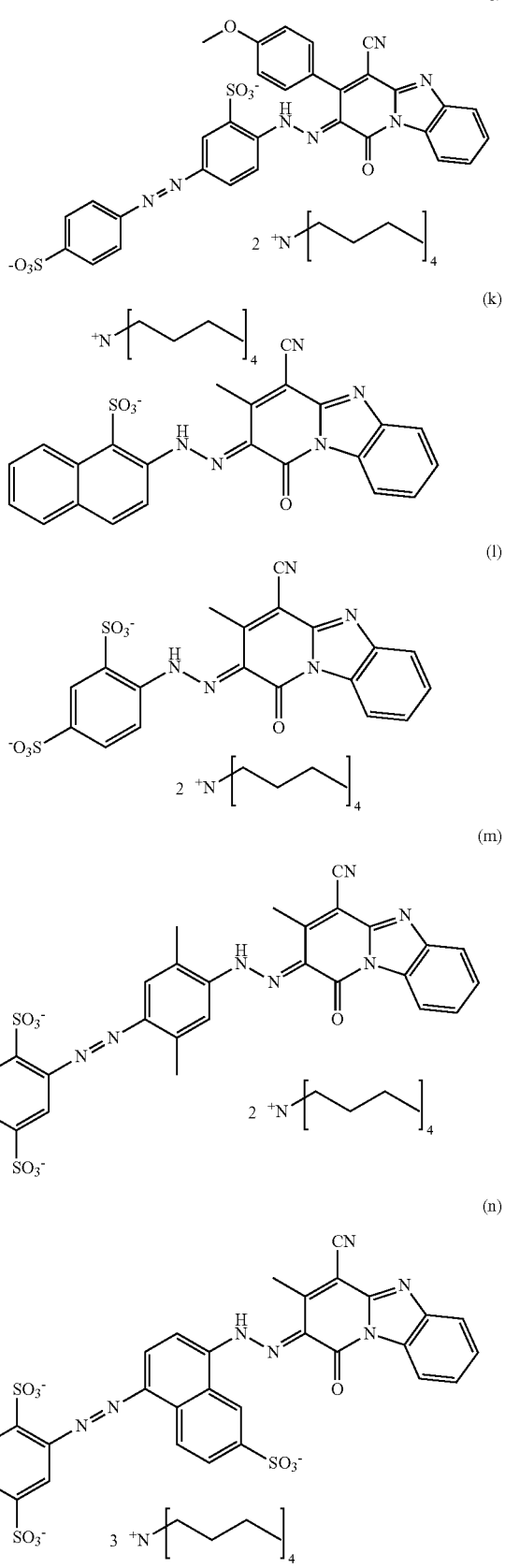

-continued
(o)
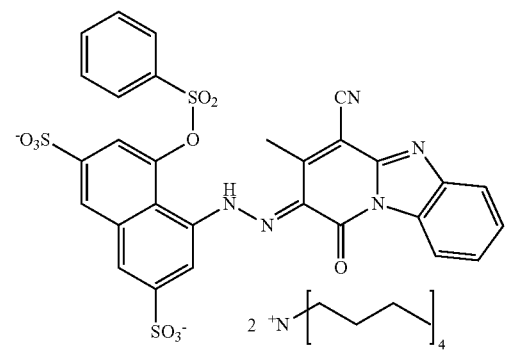
(p)
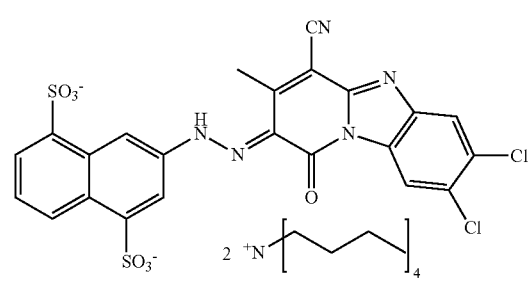
(q)
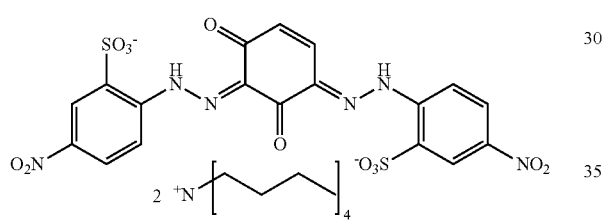
(r)
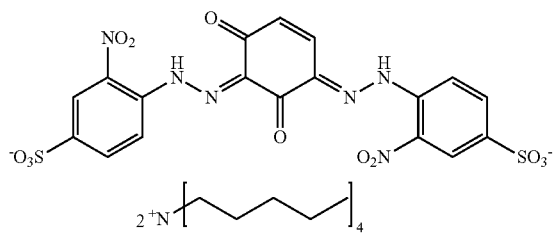
-continued
(s)
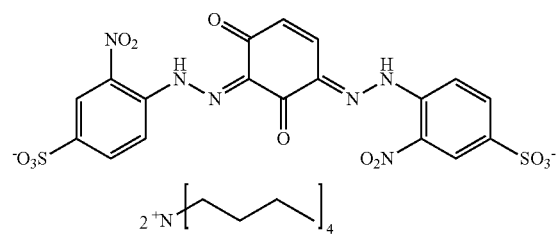
(t)
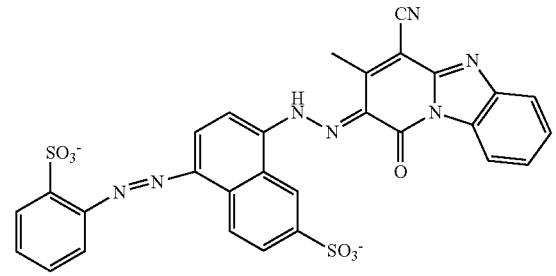
(u)
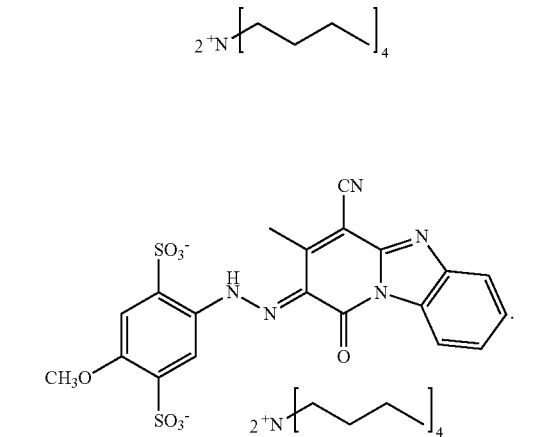
* * * * *

UNITED STATES PATENT AND TRADEMARK OFFICE
CERTIFICATE OF CORRECTION

PATENT NO. : 9,968,534 B2
APPLICATION NO. : 13/988153
DATED : May 15, 2018
INVENTOR(S) : Andrew Greaves Page 1 of 1

It is certified that error appears in the above-identified patent and that said Letters Patent is hereby corrected as shown below:

In the Claims

Column 46, Line 55, Claim 17 change "a sigma a bond" to -- a sigma σ bond --.

Signed and Sealed this
Second Day of October, 2018

Andrei Iancu
*Director of the United States Patent and Trademark Office*